US009123322B2

(12) United States Patent
Kojima et al.

(10) Patent No.: US 9,123,322 B2
(45) Date of Patent: Sep. 1, 2015

(54) HOWLING SUPPRESSION DEVICE, HEARING AID, HOWLING SUPPRESSION METHOD, AND INTEGRATED CIRCUIT

(75) Inventors: Mariko Kojima, Osaka (JP); Takefumi Ura, Ehime (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 275 days.

(21) Appl. No.: 13/817,149

(22) PCT Filed: Jul. 30, 2012

(86) PCT No.: PCT/JP2012/004837
§ 371 (c)(1), (2), (4) Date: Feb. 15, 2013

(87) PCT Pub. No.: WO2013/054459
PCT Pub. Date: Apr. 18, 2013

(65) Prior Publication Data

US 2013/0272533 A1 Oct. 17, 2013

(30) Foreign Application Priority Data

Oct. 14, 2011 (JP) ................................. 2011-226439

(51) Int. Cl.

| | |
|---|---|
| ***A61F 11/06*** | (2006.01) |
| ***H04R 3/00*** | (2006.01) |
| ***H04R 25/00*** | (2006.01) |
| ***H03G 3/00*** | (2006.01) |
| ***G10K 11/16*** | (2006.01) |
| ***H04R 3/02*** | (2006.01) |

(52) U.S. Cl.
CPC *G10K 11/16* (2013.01); *H04R 3/02* (2013.01); *H04R 25/45* (2013.01)

(58) Field of Classification Search
None
See application file for complete search history.

(56) References Cited

U.S. PATENT DOCUMENTS

| | | | |
|---|---|---|---|
| 6,338,036 | B1 | 1/2002 | Miyazawa |
| 7,974,428 | B2 | 7/2011 | Klinkby et al. |

(Continued)

FOREIGN PATENT DOCUMENTS

| | | |
|---|---|---|
| EP | 2 293 595 | 3/2011 |
| JP | 2000-081891 | 3/2000 |

(Continued)

OTHER PUBLICATIONS

International Search Report issued Nov. 6, 2012 in International (PCT) Application No. PCT/JP2012/004837.

(Continued)

*Primary Examiner* — Regina N Holder
(74) *Attorney, Agent, or Firm* — Wenderoth, Lind & Ponack, L.L.P.

(57) ABSTRACT

A howling suppression device includes a subtractor which subtracts a pseudo feedback signal from an input signal; an adaptive filter which produces a pseudo feedback signal for a next input signal; and a coefficient update control unit which controls an update rate of a filter coefficient of the adaptive filter and includes: a level calculation unit which calculates a signal level of the input signal; a signal-rising-edge detection unit which detects a rising-edge point; a reverberation section detection unit which detects a reverberation section; and an update rate control unit which sets the update rate to a first rate in the reverberation section and to a second rate in other sections. The adaptive filter updates the filter coefficient at the update rate set by the update rate control unit.

10 Claims, 18 Drawing Sheets

(56) References Cited

U.S. PATENT DOCUMENTS

| | | | |
|---|---|---|---|
| 2006/0140429 | A1 | 6/2006 | Klinkby et al. |
| 2009/0067651 | A1 | 3/2009 | Klinkby et al. |
| 2010/0329474 | A1 | 12/2010 | Ura |

FOREIGN PATENT DOCUMENTS

| | | |
|---|---|---|
| JP | 2002-076999 | 3/2002 |
| JP | 2002-156997 | 5/2002 |
| JP | 2006-166375 | 6/2006 |
| JP | 2007-515820 | 6/2007 |
| JP | 2009-532924 | 9/2009 |
| WO | 2005/020632 | 3/2005 |
| WO | 2005/074156 | 8/2005 |
| WO | 2007/113282 | 10/2007 |
| WO | 2007/113283 | 10/2007 |
| WO | 2008/123062 | 10/2008 |

OTHER PUBLICATIONS

European Search Report issued Feb. 24, 2015 in corresponding European Patent Application No. 12822951.5.

(a)

(b)

(a)

(b)

HOWLING SUPPRESSION DEVICE, HEARING AID, HOWLING SUPPRESSION METHOD, AND INTEGRATED CIRCUIT

TECHNICAL FIELD

The present invention relates to a howling suppression device which automatically detects and suppresses a howling sound generated by sound coupling between a speaker and a microphone in a sound apparatus including a microphone and a speaker.

BACKGROUND ART

Howling is an oscillation phenomenon caused by a sound loop in which a sound outputted from a speaker returns to a microphone. Once a sound loop is formed, a sinusoidal signal having a sharp peak is generated and a sound having a particular frequency continues to be amplified until the loop is cut.

As a conventional howling suppression device, there is proposed one which estimates spatial transfer characteristics between a microphone and a speaker by adaptive processing using an adaptive filter, and cuts a sound loop by subtracting a pseudo feedback signal produced by the adaptive filter from an input signal, thereby suppressing a howling sound (see Patent Literature 1 for an example).

CITATION LIST

Patent Literature

[PTL 1] Japanese Unexamined Patent Application Publication (Transition of PCT Application) No. 2009-532924

SUMMARY OF INVENTION

Technical Problem

However, such a conventional howling suppression device has a problem that the estimation performance of the spatial transfer characteristics of the adaptive filter may decline, or sound quality of a processed sound may be degraded for reasons such as erroneous detection of howling components included in a sound picked up by a microphone.

The present invention has its object to provide a howling suppression device which has increased accuracy in detection of howling caused by audio feedback, and adaptively suppresses the howling, thereby solving the problem of the conventional art.

Solution to Problem

A howling suppression device according to an aspect of the present invention reduces a howling component included in an input signal. Specifically, the howling suppression device includes: a subtractor which produces an error signal by subtracting, from the input signal, a pseudo feedback signal which is an estimated signal of a feedback signal included in the input signal as the howling component; an adaptive filter which produces a pseudo feedback signal by applying filtering to the error signal, the produced pseudo feedback signal being to be used for a next input signal; and a coefficient update control unit configured to control an update rate of a filter coefficient of the adaptive filter. The coefficient update control unit includes: a level calculation unit configured to calculate a signal level of the input signal; a signal-rising-edge detection unit configured to detect a rising-edge point from which an increase amount of the signal level of the input signal per unit time exceeds a threshold value; a reverberation section detection unit configured to detect a reverberation section which starts at the rising-edge point and ends at a terminal point at which the signal level of the input signal departs from a predetermined range which gradually narrows with time; and an update rate control unit configured to set the update rate in the reverberation section to a first rate and the update rate in a section other than the reverberation section to a second rate which is higher than the first rate. The adaptive filter updates the filter coefficient for the application of the filtering to the error signal at the update rate set by the update rate control unit.

It should be noted that these general or specific aspects of the present invention can be implemented as a system, a method, an integrated circuit, a computer program, a recording medium, or any combination of a system, a method, an integrated circuit, a computer program, and a recording medium.

Advantageous Effects of Invention

According to the present invention, it is possible to increase accuracy in detection of howling caused by audio feedback, and adaptively suppress the howling.

DESCRIPTION OF EMBODIMENTS

Underlying Knowledge Forming Basis of the Present Invention

Figure 19:
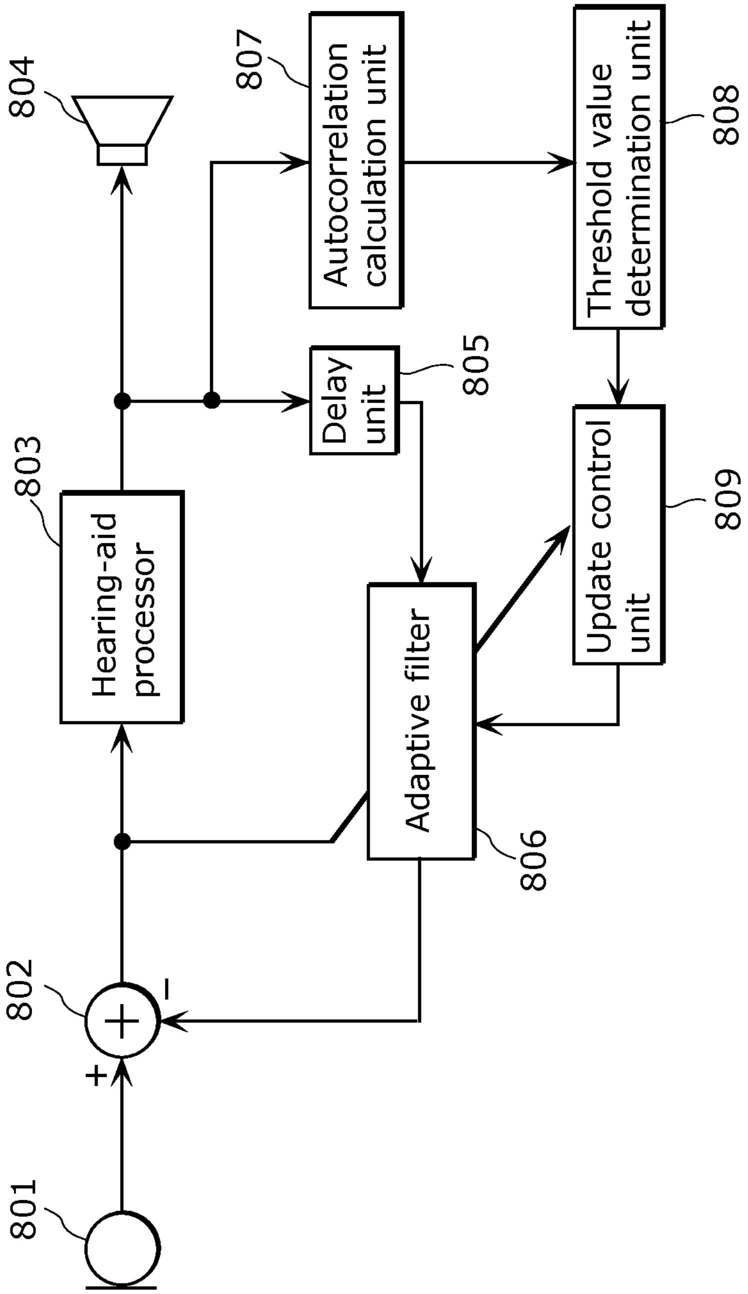
FIG. 19 is a block diagram showing of a howling suppression device described in PTL 1.

FIG. 19 is a block diagram showing the configuration of a howling suppression device described in PTL 1.

In FIG. 19, the howling suppression device includes: a microphone 801 which converts an input sound into an input signal; a subtractor 802 which subtracts an output signal of an adaptive filter 806 from the input signal of the microphone 801 to output an error signal; a hearing-aid processor 803 which produces a processor output signal by applying an amplification gain to the error signal; a speaker 804 which converts the output signal of the hearing-aid processor 803 into an output sound; a delay unit 805 which delays the output signal of the hearing-aid processor 803; an adaptive filter 806 which adaptively derives an adaptive filter output signal (a pseudo feedback signal) by applying a filter coefficient to an output signal of the delay unit 805; an autocorrelation calculation unit 807 which calculates an autocorrelation of the output signal of the hearing-aid processor 803; a threshold value evaluation unit 808 which evaluates the value of autocorrelation calculated by the autocorrelation calculation unit 807 based on a threshold value to determine a change of adaptation rate; and an update control unit 809 which determines an update rate of the adaptive filter 806 from the determination result of the threshold value evaluation unit 808.

The signal inputted from the microphone 801 passes through the hearing-aid processor 803 to be amplified and is outputted from the speaker 804. At this time, part of the output signal of the speaker 804 is inputted again to the microphone 801 as a feedback signal. Then, the loop of a sound is maintained and the sound is repeatedly amplified in the hearing-aid processor 803, so that howling, which is an oscillation phenomenon of signal, occurs. Accordingly, by causing the adaptive filter 806 to estimate the spatial transfer characteristics between the speaker 804 and the microphone 801 to produce a pseudo feedback signal which is an estimated feedback signal to which the howling is attributed, and subtracting the estimated pseudo feedback signal from the input signal at the subtractor 802, it is possible to suppress the howling.

The adaptive filter 806 has a property to preferentially estimate a signal having a stronger autocorrelation. That is, upon input of a sinusoidal signal, the adaptive filter proceeds with updating so as to simulate the characteristics of the sinusoidal signal. The algorithm for updating the filter characteristics of the adaptive filter 806 works so as to make the error signal after passing through the subtractor 802 smaller. When the adaptive filter 806 proceeds with the updating so as to cancel the sinusoidal signal, distortion in the signal increases as the adaptive filter 806 further proceeds with the updating. This significantly deteriorates sound quality and causes howling. Therefore, for such an input signal, it is necessary to contrive ways and means to prevent distortion in an output signal by, for example, stopping or slowing down updating of the adaptive filter 806. Accordingly, the howling suppression device of PTL 1 has a configuration which temporarily suspends the updating when it is determined from an autocorrelation vale of a signal that a pure tone is present in the input signal.

In this way, the howling suppression device described in PTL 1 controls updating of the adaptive filter 806 by evaluating autocorrelation of a signal based on a threshold value, and temporarily suspends the updating of the adaptive filter 806 when a pure sound is detected, thereby allowing the suppression of breakdown of the filter coefficient of the adaptive filter 806.

However, in the configuration of PTL 1, since a pure sound is detected only based on autocorrelation of a signal, there is a problem that a signal to be essentially suppressed and has a high autocorrelation, such as a signal of a howling sound, may be erroneously determined and therefore the adaptive filter 806 is erroneously updated, which may result in failure in cancelling of a sound to be essentially suppressed and deterioration of sound quality.

In order to solve the problem, provided is a howling suppression device according to an aspect of the present invention reduces a howling component included in an input signal. Specifically, the howling suppression device includes: a subtractor which produces an error signal by subtracting, from the input signal, a pseudo feedback signal which is an estimated signal of a feedback signal included in the input signal as the howling component; an adaptive filter which produces a pseudo feedback signal by applying filtering to the error signal, the produced pseudo feedback signal being to be used for a next input signal; and a coefficient update control unit configured to control an update rate of a filter coefficient of the adaptive filter. The coefficient update control unit includes: a level calculation unit configured to calculate a signal level of the input signal; a signal-rising-edge detection unit configured to detect a rising-edge point from which an increase amount of the signal level of the input signal per unit time exceeds a threshold value; a reverberation section detection unit configured to detect a reverberation section which starts at the rising-edge point and ends at a terminal point at which the signal level of the input signal departs from a predetermined range which gradually narrows with time; and an update rate control unit configured to set the update rate in the reverberation section to a first rate and the update rate in a section other than the reverberation section to a second rate which is higher than the first rate. The adaptive filter updates the filter coefficient for the application of the filtering to the error signal at the update rate set by the update rate control unit.

The present configuration makes it possible to reduce the erroneous adaptation of the adaptive filter and corresponding deterioration in quality of processed sound by detecting a transient signal by signal-rising-edge detection using the signal level of an input signal, and detecting a sinusoidal signal by signal section detection to decrease the update rate of the adaptive filter from the normal update rate. Note that "update of the filter coefficient of the adaptive filter" may be expressed as "update of the adaptive filter" in the present description.

The coefficient update control unit may further include a level determination unit configured to determine, on a per-unit time basis in the reverberation section, whether or not the signal level of the input signal exceeds a predetermined value. In the reverberation section, the update rate control unit may be configured to set the update rate to the first rate while the signal level of the input signal exceeds the predetermined value, and to the second rate while the signal level of the input signal is equal to or below the predetermined value.

The present configuration allows the update rate of the filter coefficient of the adaptive filter to be adaptively adjusted according to the magnitude of the level of an input signal.

The coefficient update control unit may further include: a frequency analysis unit configured to convert the signal level of the input signal into a frequency signal; and a peak detection unit configured to determine whether or not the frequency signal has a peak. When the frequency signal has a plurality of the peaks, the update rate control unit may be configured to set the update rate in the reverberation section to the first rate, and set the update rate in a section other than the reverberation section to the second rate.

The present configuration allows the determination of a sinusoidal signal to be performed by analyzing the frequency characteristics of an input signal so that the update control of the adaptive filter can be performed more accurately.

As an example, the signal-rising-edge detection unit may be configured to detect the rising-edge point by comparing a gradient value of the signal level of the input signal in time direction with the threshold value.

The gradient value in time direction of the signal level is monitored as in the present configuration, so that the update control of the adaptive filter can be performed more accurately.

As an example, the signal-rising-edge detection unit may be configured to detect the rising-edge point by comparing a differential value of the signal level of the input signal in time direction with the threshold value.

The differential value in time direction of the signal level is monitored as in the present configuration, so that the update control of the adaptive filter can be performed more accurately.

The reverberation section detection unit may further include: a maximum value calculation unit configured to gradually decrease a maximum value of the predetermined range with time; and a reverberation section determination unit configured to determine a point at which the signal level of the input signal reaches the maximum value as the terminal point of the reverberation section.

The present configuration allows a reverberation section of a sinusoidal signal to be determined by comparing a gradually decreasing maximum value hold with a signal level, so that the update control of the adaptive filter can be performed more accurately.

The reverberation section detection unit may further include: a minimum value calculation unit configured to gradually increase a minimum value of the predetermined range with time; and a reverberation section determination unit configured to determine a point at which the signal level of the input signal reaches the minimum value as the terminal point of the reverberation section.

The present configuration allows the reverberation section of a sinusoidal signal to be determined by comparing a gradually increasing minimum value hold with a signal level, so that the update control of the adaptive filter can be performed more accurately.

A hearing aid according to an aspect of the present invention includes: any one of the above-described howling suppression devices; and an output unit configured to convert the error signal produced by the subtractor into an output sound and output the output sound.

A hearing aid in this configuration causes less discomfort due to howling.

A howling suppression method according to an aspect of the present invention is a method for reducing a howling component included in an input signal. Specifically, the howling suppression method includes: producing an error signal by subtracting, from the input signal, a pseudo feedback signal which is an estimated signal of a feedback signal included in the input signal as the howling component; producing a pseudo feedback signal by applying filtering to the error signal, the produced pseudo feedback signal to be used for a next input signal; and controlling an update rate of a filter coefficient for the producing of a pseudo feedback signal. The controlling includes: calculating a signal level of the input signal; detecting a rising-edge point from which an increase amount of the signal level of the input signal per unit time exceeds a threshold value; detecting a reverberation section which starts at the rising-edge point and ends at a terminal point at which the signal level of the input signal departs from a predetermined range which gradually narrows with time; and setting the update rate in the reverberation section to a first rate and the update rate in a section other than the reverberation section to a second rate which is higher than the first rate. In the producing of a pseudo feedback signal, the filter coefficient for the application of the filtering to the error signal is updated at the update rate set by the update rate control unit.

An integrated circuit according to an aspect of the present invention reduces a howling component included in an input signal. Specifically, the integrated circuit includes: a subtractor which produces an error signal by subtracting, from the input signal, a pseudo feedback signal which is an estimated signal of a feedback signal included in the input signal as the howling component; an adaptive filter which produces a pseudo feedback signal by applying filtering to the error signal, the produced pseudo feedback signal being to be used for a next input signal; and a coefficient update control unit configured to control an update rate of a filter coefficient of the adaptive filter. The coefficient update control unit includes: a level calculation unit configured to calculate a signal level of the input signal; a signal-rising-edge detection unit configured to detect a rising-edge point from which an increase amount of the signal level of the input signal per unit time exceeds a threshold value; a reverberation section detection unit configured to detect a reverberation section which starts at the rising-edge point and ends at a terminal point at which the signal level of the input signal departs from a predetermined range which gradually narrows with time; and an update rate control unit configured to set the update rate in the reverberation section to a first rate and the update rate in a section other than the reverberation section to a second rate which is higher than the first rate. The adaptive filter updates the filter coefficient for the application of the filtering to the error signal at the update rate set by the update rate control unit.

It should be noted that these general or specific aspects of the present invention can be implemented as a system, a method, an integrated circuit, a computer program, a recording medium, or any combination of a system, a method, an integrated circuit, a computer program, and a recording medium.

Embodiments of the present invention will be described below with reference to drawings. Each of the exemplary embodiments described below shows a specific example of the present invention. The values, materials, constituent elements, layout and connection of the constituent elements, steps, and the order of the steps in the embodiments are given not for limiting the present invention but merely for illustrative purposes only. Therefore, among the structural elements in the following exemplary embodiments, structural elements not recited in any one of the independent claims are described as arbitrary structural elements.

Embodiment 1

A howling suppression device according to Embodiment 1 includes: a subtractor which produces an error signal by subtracting, from the input signal, a pseudo feedback signal which is an estimated signal of a feedback signal included in the input signal as the howling component; an adaptive filter which produces a pseudo feedback signal by applying filtering to the error signal, the produced pseudo feedback signal being to be used for a next input signal; and a coefficient update control unit configured to control an update rate of a filter coefficient of the adaptive filter. The adaptive filter updates the filter coefficient for the application of the filtering to the error signal at the update rate set by the coefficient update control unit (or an update rate control unit described later).

Figure 1:
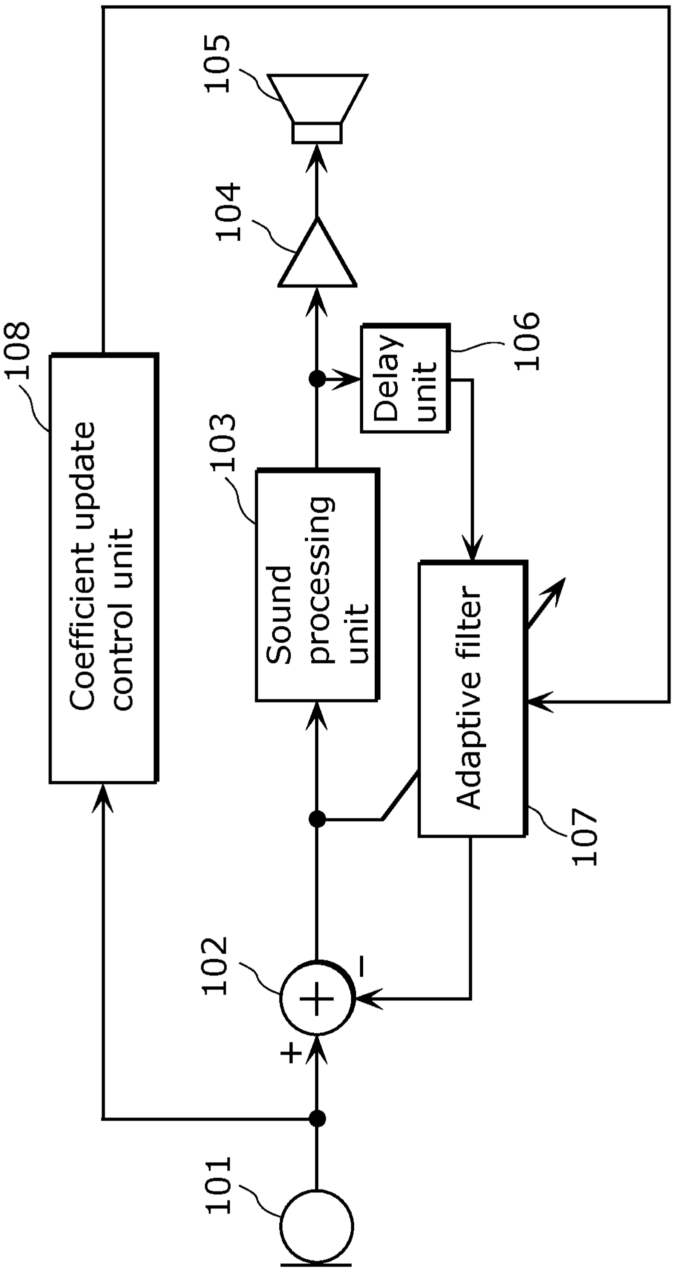
FIG. 1 is a basic block diagram of a howling suppression device in Embodiment 1.

Referring to FIG. 1, the howling suppression device according to Embodiment 1 will be described in detail. FIG. 1 is a basic block diagram of the howling suppression device in Embodiment 1.

In FIG. 1, the howling suppression device according to the present embodiment includes: a microphone 101 which picks up and converts a sound in the surrounding into an input signal (target signal); a subtractor 102 which subtracts an output signal (pseudo feedback signal) of an adaptive filter 107 from the output signal (target signal) of the microphone 101 to output an erroneous signal (error signal); a sound processing unit 103 which applies sound signal processing to an inputted error signal to output the error signal; an amplifier 104 which amplifies an output signal of the sound processing unit 103; a speaker 105 which outputs a sound (output sound) amplified by the amplifier 104; a delay unit 106 which delays the output signal of the sound processing unit 103 to output the output signal as a reference signal of the adaptive filter 107; an adaptive filter 107 which outputs a pseudo feedback signal by convoluting a filter coefficient into the inputted reference signal, and updates the filter coefficient according to an adaptation algorithm; and a coefficient update control unit 108 which determines the update rate of the adaptive filter 107 based on the target signal outputted from the microphone 101.

The coefficient update control unit according to Embodiment 1 includes: a level calculation unit configured to calculate a signal level of the input signal; a signal-rising-edge detection unit configured to detect a rising-edge point from which an increase amount of the signal level of the input signal per unit time exceeds a threshold value; a reverberation section detection unit configured to detect a reverberation section which starts at the rising-edge point and ends at a terminal point at which the signal level of the input signal departs from a predetermined range which gradually narrows with time; and an update rate control unit configured to set the update rate in the reverberation section to a first rate and the update rate in a section other than the reverberation section to a second rate which is higher than the first rate.

Figure 2:
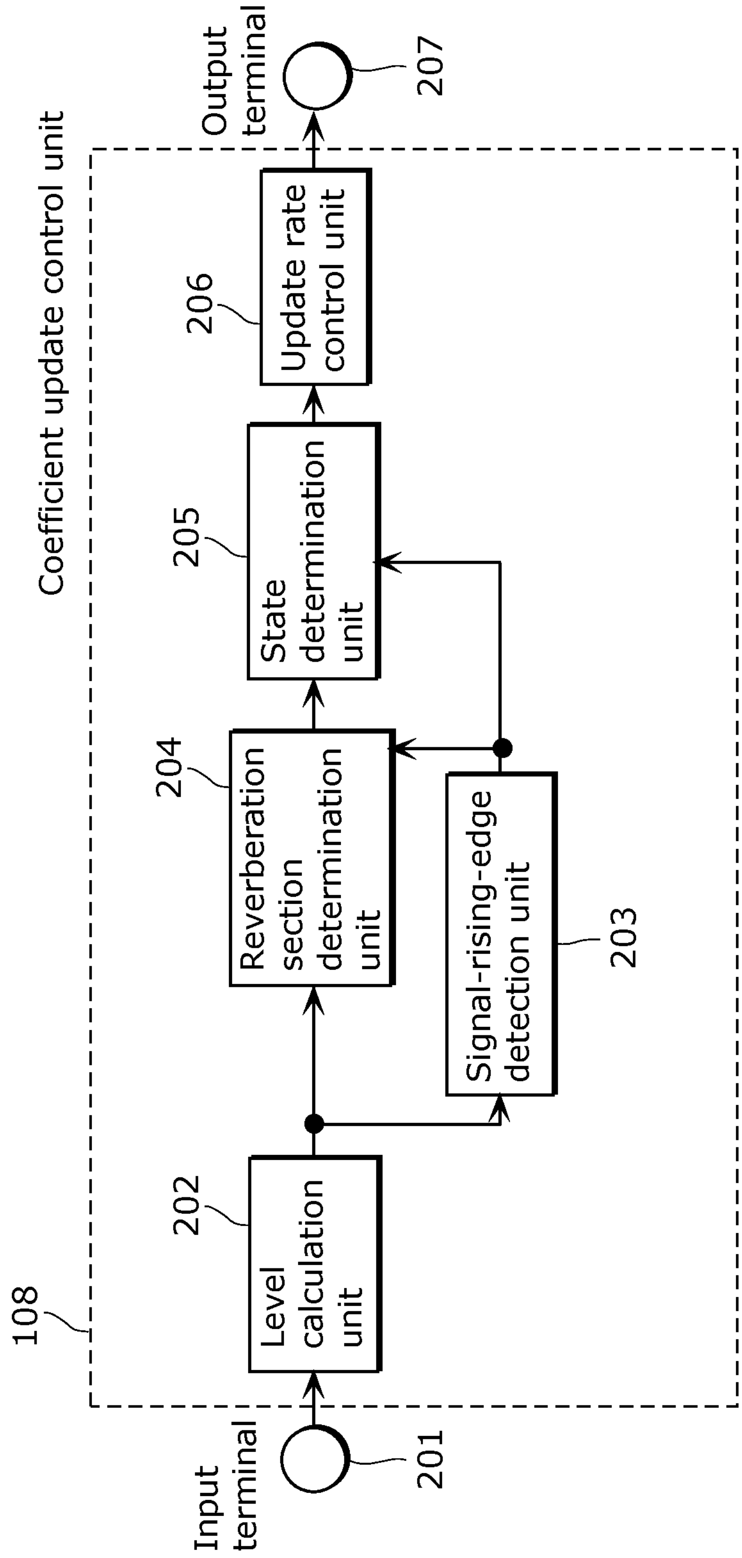
FIG. 2 is a detailed block diagram of a coefficient update control unit of the howling suppression device in Embodiment 1.

Next, referring to FIG. 2, the coefficient update control unit 108 will be described in detail. FIG. 2 is a detailed block diagram of the coefficient update control unit 108 of the howling suppression device in Embodiment 1.

In FIG. 2, the coefficient update control unit 108 according to the present embodiment includes: an input terminal 201 to which a target signal is inputted; a level calculation unit 202 which calculates a signal level of the target signal; a signal-rising-edge detection unit 203 which analyzes the strength of a rising-edge of a signal by analyzing a temporal change in an output signal of the level calculation unit 202; a reverberation section detection unit 204 which determines a reverberation section in a sinusoidal signal based on an output of the signal-rising-edge detection unit 203 and a signal level which is an output of the level calculation unit 202; a state determination unit 205 which determines whether or not a signal not suitable for the update of the filter coefficient of the adaptive filter 107 is included in the input signal, from an output result of the signal-rising-edge detection unit 203 and an output result of the reverberation section detection unit 204; an update rate control unit 206 which determines the update rate of the filter coefficient of the adaptive filter 107 according to the determination result of the state determination unit 205; and an output terminal 207 which outputs the determined update rate.

First, overall operation of the howling suppression device in Embodiment 1 will be described.

The input signal inputted to the microphone 101 is converted from an analog signal to a digital signal by an A-D convertor not shown, and thereafter the subtractor 102 subtracts an output signal (pseudo feedback signal) of the adaptive filter 107 from the input signal to obtain an error signal to be inputted to a sound processing unit 103. The sound processing unit 103, which is configured to apply a desired sound signal processing to the inputted error signal, performs processing, for example, amplification and filtering, on the error signal to output a temporal waveform. The output signal of the sound processing unit 103 is inputted to the delay unit 106, and is converted from a digital signal to an analog signal by a D-A convertor not shown, thereafter being inputted to the amplifier 104 and amplified. Then, the amplified output signal is outputted from the speaker 105 as an output sound.

At this time, a sound loop is formed between the speaker 105 and the microphone 101 as a result of feedback of part of the output sound from the speaker to the microphone 101. When the sound loop is maintained and a signal continues to go around the sound loop, the signal oscillates in a particular frequency band, causing howling. Then, the howling suppression device in Embodiment 1 suppresses the howling by means of the adaptive filter 107.

Moreover, the output signal outputted from the sound processing unit 103 is inputted to the delay unit 106 to be delayed by, for example, several to several tens of samples. The output signal delayed by the delay unit 106 is outputted to the adaptive filter 107 as a reference signal. Then, the adaptive filter 107 convolutes a filter coefficient into a reference signal acquired from the delay unit 106, and outputs a pseudo feedback signal to the subtractor 102. The subtractor 102 subtracts the pseudo feedback signal from a microphone input signal (target signal), thereby eliminating a feedback component (howling component) included in the target signal, and outputs an error signal.

The adaptive filter 107 is, for example, a FIR filter with 256 taps. The filter coefficient of the adaptive filter 107 is updated, for example, using an adaptive algorithm which operates under a criterion to minimize a mean square error between the target signal and the error signal. As the algorithm for updating the adaptive filter 107, various known adaptive algorithms, such as an NLMS algorithm are used. The mean square error is minimized when the adaptive filter 107 accurately estimate the spatial transfer characteristics.

In this configuration, proceeding with updating of the filter coefficient increases accuracy in estimation of the spatial transfer characteristics by the adaptive filter 107, and the adaptive filter 107 outputs a pseudo feedback signal proximate to a feedback signal. As a result, since the pseudo feedback signal is removed from the target signal, the error signal outputted from the subtractor 102 can provide a sound which the user originally wants to hear. Note that in FIG. 1, although the delay unit 106 receives the output signal of the sound processing unit 103 as an input, the delay unit 106 may be configured to receive, as an input, the output signal (error signal) of the subtractor 102 or the output signal of the amplifier 104.

Next, operation of the coefficient update control unit 108 in Embodiment 1 will be described. The coefficient update control unit 108 is provided to perform control of the update of the filter coefficient of the adaptive filter 107.

The input terminal 201 receives input of the input signal (target signal) of the microphone 101. The level calculation unit 202 calculates a signal level of the target signal inputted to the input terminal 201. The signal-rising-edge detection unit 203 monitors the magnitude of the change in time direction of the signal level calculated by the level calculation unit 202. The signal-rising-edge detection unit 203 is provided to monitor the amount of change in the level of an input signal in order to detect the input signal as a transient signal when the input signal has a sharp rising-edge in time direction. The transient signal is characterized by its very high signal level over the entire frequency band, and has a property of reducing accuracy in estimation of the spatial transfer characteristics by the adaptive filter 107.

Figure 3:
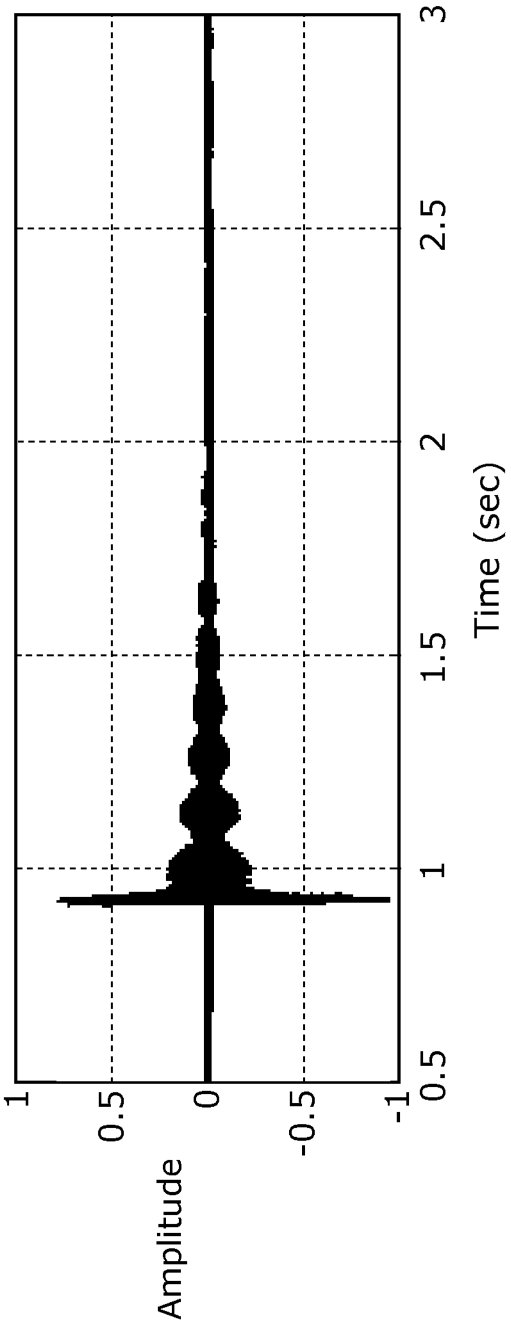
FIG. 3 is a graph showing an example of a time waveform of a sinusoidal signal.

FIG. 3 is a graph showing an example of a time waveform of a sinusoidal signal for which updating the adaptive filter 107 is not appropriate. In FIG. 3, a sinusoidal signal is generated around 0.9 seconds from the start and lasts for approximately 2 seconds. To be specific, it is observed that a sharp rising-edge (transient signal) occurs around 0.9 seconds from the start and is followed by a reverberation with its energy gradually attenuating.

Figure 4:
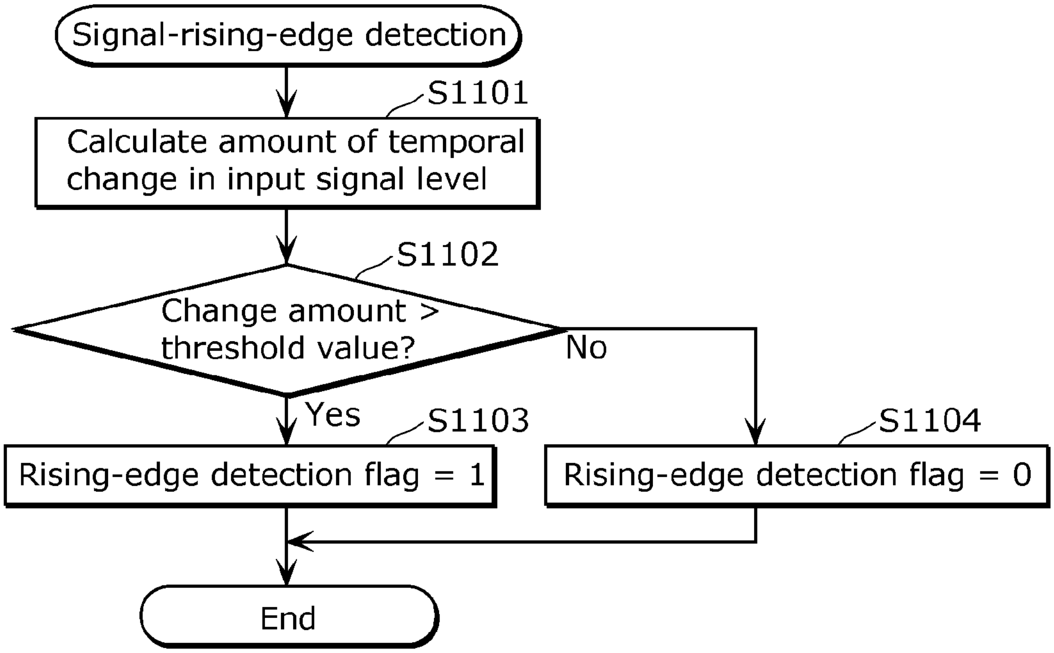
FIG. 4 is a flowchart illustrating operation of a signal-rising-edge detection unit of the howling suppression device in Embodiment 1.

FIG. 4 is a flowchart illustrating operation of the signal-rising-edge detection unit 203 in FIG. 2. First, the signal-rising-edge detection unit 203 calculates the amount of temporal change in the signal level of an input signal from the signal level of the input signal at the present time (t) and the signal level of the input signal at a time (t−n) (S1101). Here, it is assumed that a gradient between the two points in time is calculated as the amount of temporal change. Next, the signal-rising-edge detection unit 203 determines the magnitude relationship between the gradient calculated in step S1101 and a predetermined threshold value (S1102). When the gradient is greater than the threshold value (S1102, Yes), the signal-rising-edge detection unit 203 sets a rising-edge detection flag to 1 (S1103). When the gradient is less than or equal to a threshold value (S1102, No), the signal-rising-edge detection unit 203 sets the rising-edge detection flag to 0 (S1104).

Here, a signal of a howling sound takes several hundreds milliseconds to rise up. In contrast to this, a transient signal (the leading portion of a sinusoidal signal), which takes several milliseconds to several tens of milliseconds to rise up, is a signal which takes a short time to rise up compared with the signal of a howling sound. This means that a value smaller than the time taken by a howling sound to rise up is set for the threshold value to be used in Step S1102.

Note that the above-described set values of the rising-edge detection flag are merely examples, and the present invention will not be limited to this. Specifically, the rising-edge detection flag may be set to either a value ("1" in the above described example) which indicates a detection of a rising-edge point at which the increase amount per unit time of the signal level of the input signal exceeds a threshold value, or a value ("0" in the above described example) which indicates detection of no rising-edge position. The same applies to the values to be set for other flags described below.

The reverberation section detection unit according to Embodiment 1 includes a maximum value calculation unit configured to gradually decrease a maximum value of a predetermined range with time, and a reverberation section determination unit configured to determine a point at which the signal level of the input signal reaches the maximum value as a terminal point of a reverberation section. Note that for Embodiment 1, description will be made on an example in which a minimum value of a predetermined range is kept constant and a maximum value of the predetermined range is gradually decreased so as to gradually narrow the predetermined range with time.

Figure 5:
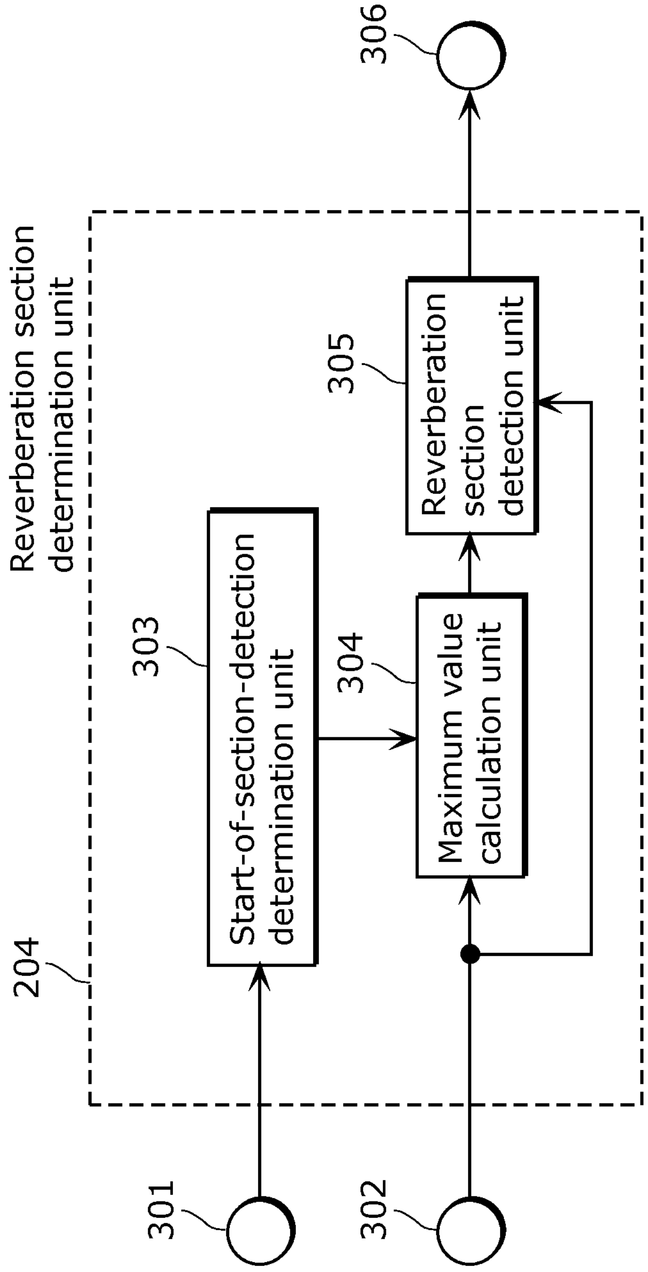
FIG. 5 is a detailed block diagram of a reverberation section detection unit of the howling suppression device in Embodiment 1.

Referring to FIG. 5, the reverberation section detection unit according to Embodiment 1 will be described in detail. FIG. 5 is a detailed block diagram of the reverberation section detection unit 204 in FIG. 2.

In FIG. 2, the reverberation section detection unit 204 according to Embodiment 1 includes: an input terminal 301 to which a rising-edge detection flag is inputted; an input terminal 302 to which a signal level of an input signal is inputted; a start-of-section-detection determination unit 303 which determines whether or not to perform detection of a reverberation section from the value of the rising signal detection flag, and outputs a determination result; a maximum value calculation unit 304 which calculates a maximum value of a signal level inputted from the input terminal 302 according to the determination result at the start-of-section-detection determination unit 303; a reverberation section determination unit 305 which determines a reverberation section from the input terminal 302 and the maximum value outputted from the maximum value calculation unit 304; and an output terminal 306 which outputs a determination result of the reverberation section determination unit 305.

Figure 6:
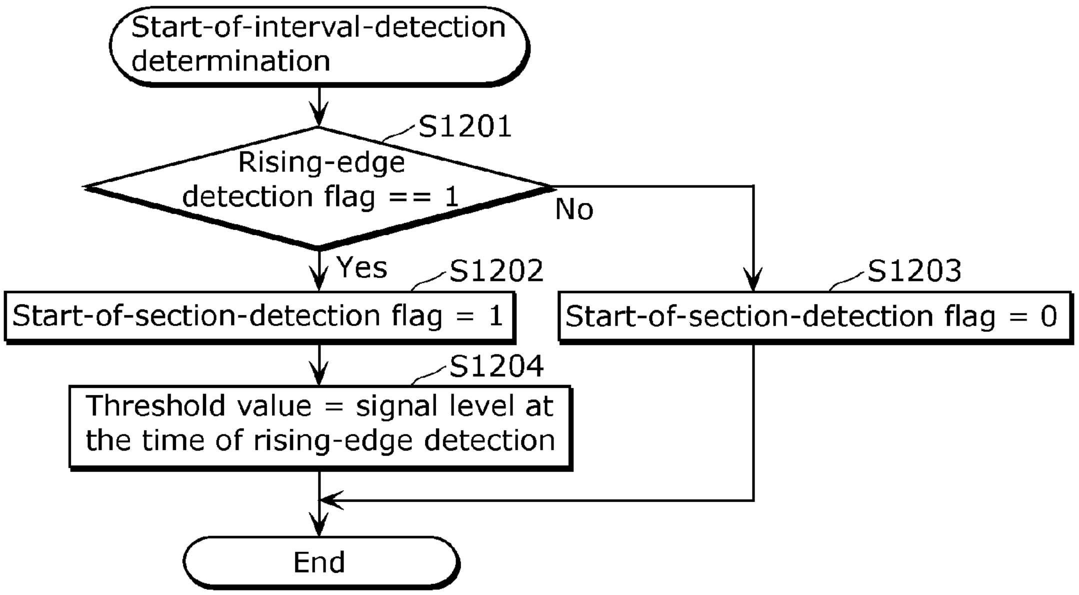
FIG. 6 is a flowchart illustrating operation of a signal section detection unit of the howling suppression device in Embodiment 1.
Figure 6:
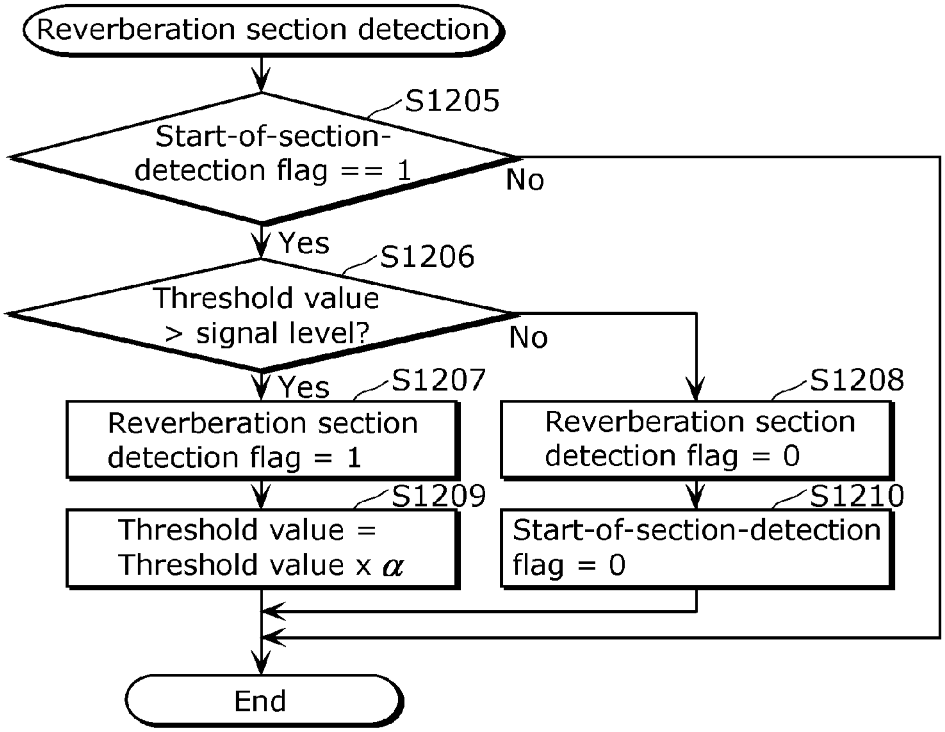

FIG. 6 is a flowchart illustrating operation of the reverberation section detection unit 204 in FIG. 2. First, the reverberation section detection unit 204 determines whether or not to start detection of a reverberation section as shown in (a) of FIG. 6. At the beginning the start-of-section-detection determination unit 303 determines whether or not the value of a rising-edge detection flag is 1 (S1201). When the value of the rising-edge detection flag is 1 (S1201, Yes), the start-of-section-detection determination unit 303 sets a start-of-section-detection flag to 1 (S1202). When the value of the rising-edge detection flag is 0 (S1201, No), the start-of-section-detection determination unit 303 sets the start-of-section-detection flag to 0 (S1203). Moreover, when the value of the rising-edge detection flag is 1, the maximum value calculation unit 304 sets, as a threshold value (a maximum value of a predetermined range), the signal level at the time of detection of a rising-edge point (S1204).

Next, the reverberation section detection unit 204 performs detection of a reverberation section as shown in (b) of FIG. 6. First, the reverberation section determination unit 305 checks the value of the start-of-section-detection flag (S1205). The value has been determined in (a) of FIG. 6. When the value of the start-of-section-detection flag is 0 (S1205, No), the reverberation section determination unit 305 ends the processing without determining a reverberation section. When the value of the start-of-section-detection flag is 1 (S1205, Yes), the reverberation section determination unit 305 compares the signal level at the present time of the input signal acquired from the level calculation unit 202 with the threshold value set in step S1204 of (a) of FIG. 6 to determine a reverberation section (S1206).

Next, when the threshold value is above the signal level of the input signal at the present time (S1206, Yes), the reverberation section determination unit 305 sets the value of the reverberation section detection flag to 1 (S1207). Moreover, the reverberation section determination unit 305 multiplies the threshold value by a constant α which is less than 1 to make it a new threshold value for the next step (S1209). When the threshold value is below the signal level of the input signal at the present time (S1206, No), the reverberation section determination unit 305 sets the value of the reverberation section detection flag to 0 (S1208). In this case, the reverberation section determination unit 305 determines that the reverberation section has ended, and sets the value of the start-of-section-detection flag to 0 (S1210).

Here, the signal level of a howling sound increases or remains at the same level (that is, the howling sound does not attenuate) with time unless it is suppressed by the adaptive filter 107. When it is suppressed by the adaptive filter 107, the signal level rapidly attenuates in tens to hundreds of milliseconds. In contrast to this, it takes approximately several hundreds of milliseconds to several seconds for a sinusoidal signal to attenuate. In other words, the value of a in step S1209 may be set such that the decreasing rate of the maximum value of the predetermined range is higher than the attenuation rate of a howling sound which is not suppressed by the adaptive filter 107 and lower than the attenuation rate of a howling sound which is suppressed by the adaptive filter 107.

Figure 7:
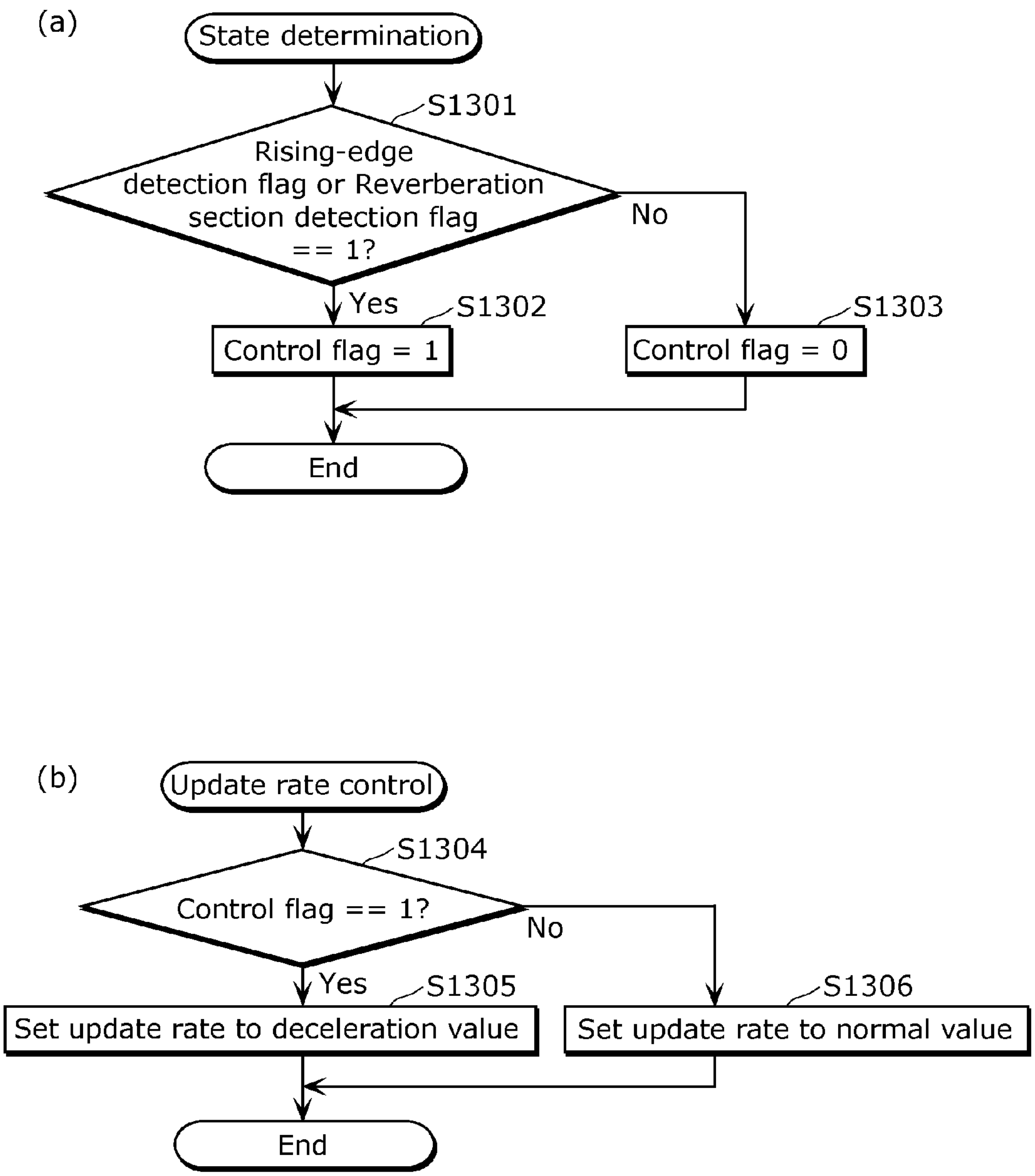
FIG. 7 is a flowchart illustrating operation of a state determination unit and an update rate control unit of the howling suppression device in Embodiment 1.

FIG. 7 is a flowchart illustrating operation of the state determination unit 205 and the update rate control unit 206 in FIG. 2. In the state determination unit 205, as shown in (a) of FIG. 7, when at least one of the inputted rising-edge detection flag and reverberation section detection flag is 1 (S1301, Yes), a control flag is set to 1 on an assumption that the update rate control is to be applied (S1302). When both values of the two flags are 0 (S1301, No), the state determination unit 205 determines that update rate control is not necessary and sets the control flag to 0 (S1303).

Note that at the moment when a transient signal occurs, the rising-edge detection flag is set to 1, and the signal interval detection flag is set to 1. While the reverberation section of a sinusoidal signal is lasting, the rising-edge detection flag is set to 0, and the signal interval detection flag is set to 1. In other words, controlling the update rate as shown in FIG. 7 makes it possible to adaptively control the update rate of the filter coefficient of the adaptive filter 107 whether a transient signal alone or a sinusoidal signal including a transient signal and a reverberation section following the transient signal occurs.

Next, the update rate control unit 206 determines the value of the control flag as shown in (b) of FIG. 7 (S1304). When the value of the control flag is 1 (S1304, Yes), the update rate control unit 206 sets the update rate of the adaptive filter 107 to a value for deceleration (a first rate) (S1305). When the value of the control flag is 0 (S1304, No), the update rate control unit 206 sets the update rate of the adaptive filter 107 to a value for normal update (a second rate) (S1306). Note that the "update rate" refers to the update amount of the filter coefficient per unit time. To be more specific, the update rate can be restated as the amount of change in the filter coefficient in one update processing.

Figure 8:
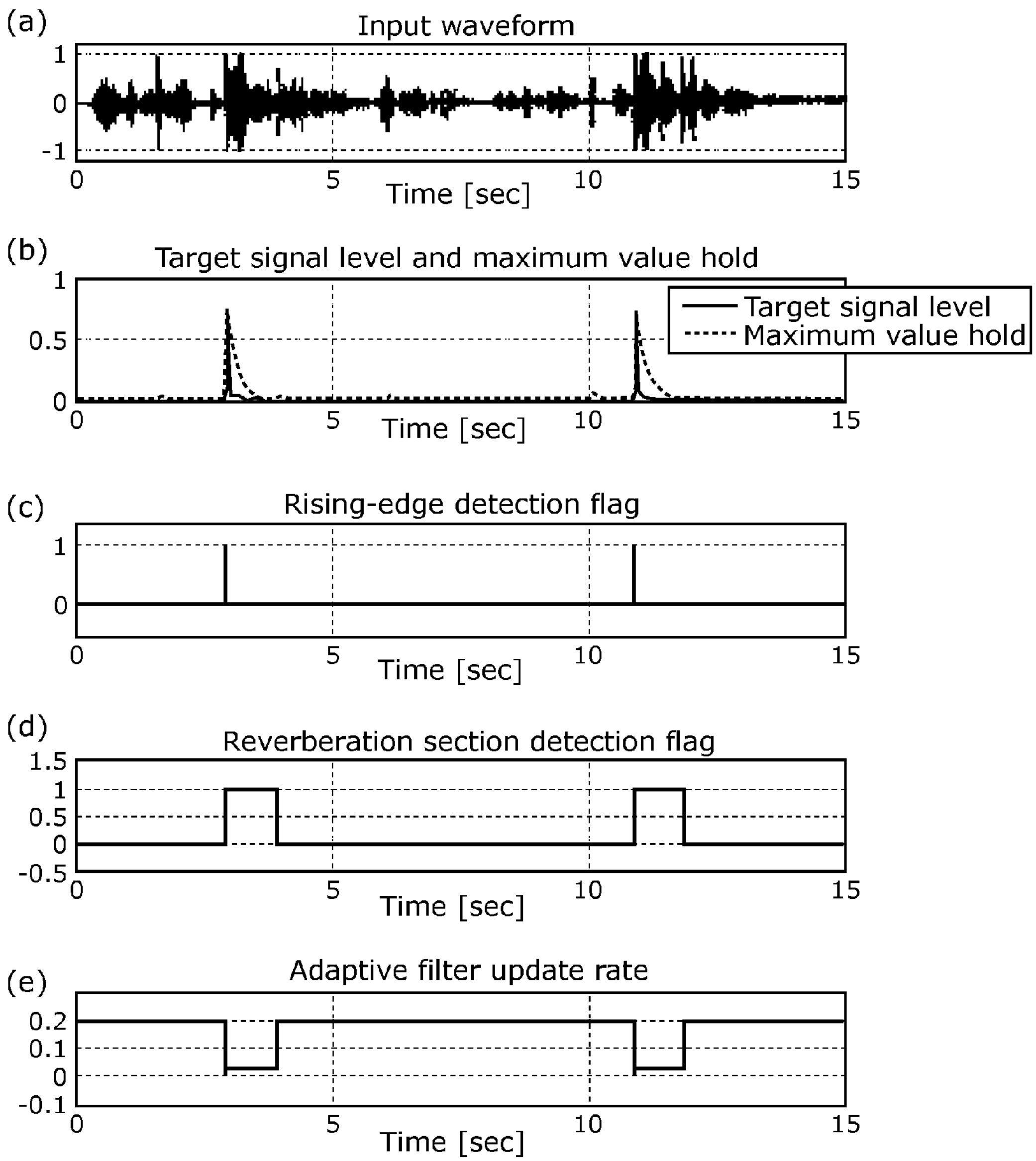
FIG. 8 is a graph illustrating procedures of update control of the howling suppression device in Embodiment 1.

FIG. 8 shows in graph form the procedures in order from detection of a transient signal to control of an update rate.

First, the signal-rising-edge detection unit 203 performs detection of a transient signal on the input signal shown in (a) of FIG. 8 to determine a starting point (rising-edge point) of a sinusoidal signal. To be specific, the signal-rising-edge detection unit 203 sets the rising-edge detection flag to 1 when a gradient value of the signal level between two different time points, time (t) and time (t−n), exceeds a predetermined threshold value, and sets the rising-edge detection flag to 0 when the gradient value is less than or equal to the threshold value. An example of transition of the rising-edge detection flag is shown in (c) of FIG. 8.

Next, the reverberation section detection unit 204 detects a reverberation section of a sinusoidal signal in particular. To be specific, the reverberation section detection unit 204 compares the signal level of a target signal calculated by the level calculation unit 202 with the value of a maximum value hold (which corresponds to a threshold value set in Step S1204 of (a) of FIG. 6 or in Step S1209 of (b) of FIG. 6) of the target signal level, as shown in (b) of FIG. 8. Since the reverberation section of a sinusoidal signal is inputted in such a way to immediately follow a transient signal, it is possible to detect a reverberation section by comparing the target signal level and the maximum value of the signal level.

To be specific, the reverberation section detection unit 204 takes advantage of the fact that the signal level in a reverberation section lowers with time to determine, as a section in which the reverberation component continues, a period in which the value of the maximum value hold and the signal level both continue to gradually decreases without a reversal in the magnitude relationship therebetween. Then, the reverberation section detection unit 204 sets the reverberation section detection flag to 1 in the section from immediately after a transient noise detection flag is turned to 1 to a reversal in the magnitude relationship between the values of the maximum value hold and the value of the signal level. An example of transition of the reverberation section detection flag is shown in (d) of FIG. 8.

The state determination unit 205 receives input of a rising-edge detection flag and a reverberation section detection flag. Although it has been already mentioned that a reverberation component of a sinusoidal signal deteriorates accuracy in estimation accuracy of spatial transfer characteristics by the adaptive filter 107 using the filter coefficient, it has been also confirmed that the accuracy in estimation of spatial transfer characteristics by the adaptive filter 107 using the filter coefficient deteriorates due to an abrupt change in the input level when a transient signal is inputted as well. Therefore, the state determination unit 205 sets the control flag to 1 such that updating of the filter coefficient is stopped or decelerated when at least one of the rising-edge detection flag and the reverberation section detection flag is 1.

Next, the update rate control unit 206 controls the update rate of the adaptive filter 107 according to the value of an inputted control flag. To be specific, the update rate control unit 206 sets the update rate of the adaptive filter 107 to 0 when the value of the control flag is 1 and the update of the filter coefficient is to be stopped, sets the update rate to a deceleration value when the update of the filter coefficient is to be decelerated, and sets the update rate to a normal value when the value of the control flag is 0. An example of transition of the update rate is shown in (e) of FIG. 8. Then, the set update rate is outputted from the output terminal 207 to the adaptive filter 107.

In this configuration, the signal-rising-edge detection unit 203 can detect a transient signal and the reverberation section detection unit 204 can detect the reverberation section of a sinusoidal signal, so that it is possible to determine that a signal for which updating of the filter coefficient of the adaptive filter 107 is not appropriate has been inputted. As a result of that, it is possible to appropriately adjust the update rate of the adaptive filter 107 in response to the input signal.

Note that in Embodiment 1, although a target signal of the adaptive filter 107 is used as the input signal to a coefficient update control unit 108, this is not limiting and, for example, an error signal of the adaptive filter 107 may be inputted.

Moreover, although it is described in Embodiment 1 that the signal-rising-edge detection unit 203 calculates a gradient value in time direction of signal energy, alternatively the signal-rising-edge detection unit 203 may calculate a differential value in time direction to make the determination.

Furthermore, although in Embodiment 1, the reverberation section detection unit 204 determines the reverberation section from a magnitude relationship between the value of the maximum value hold of the signal level and the state of attenuation of the signal level, the reverberation section detection unit 204 may make the determination in a such a way that it compares the signal level at the time of detection of a transient noise with a current signal level after the detection of the transient noise to determine a section in which the amount of attenuation of the signal level decreases to or below a constant value, for example, 10 dB as a reverberation section.

Embodiment 2

A reverberation section detection unit according to Embodiment 2 further includes a minimum value calculation unit configured to gradually increase the minimum value in a predetermined range with time, and a reverberation section determination unit configured to determine a position at which the signal level of an input signal reaches a minimum value as a terminal point of a reverberation section. Note that in Embodiment 2, description is made on an example in which a maximum value of a predetermined range is kept constant and a minimum value of the predetermined range is gradually increased so as to gradually narrow the predetermined range with time.

Figure 9:
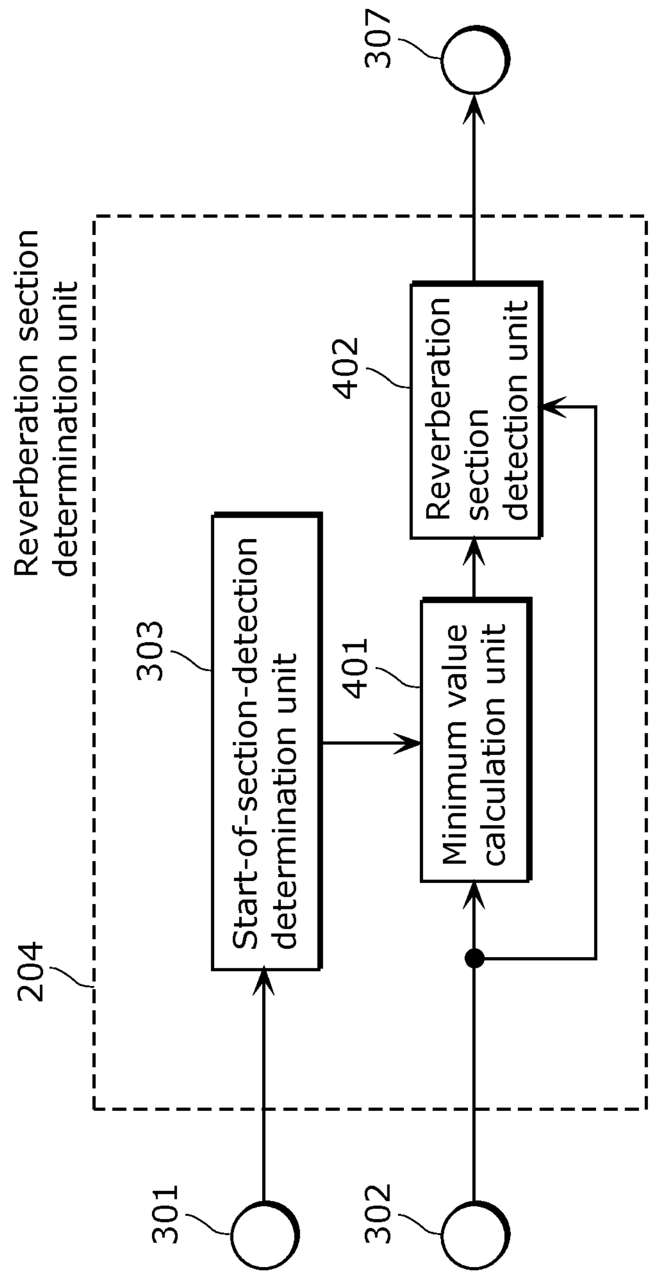
FIG. 9 is a detailed block diagram of a reverberation section detection unit of a howling suppression device in Embodiment 2.

Referring to FIG. 9, the reverberation section detection unit according to Embodiment 2 will be described in detail. FIG. 9 is a detailed block diagram of the reverberation section detection unit 204 of the howling suppression device according to Embodiment 2 of the present invention. Note that in FIG. 9, like components as those of FIG. 5 are given like reference signs thereby omitting the description thereof.

In FIG. 9, the reverberation section detection unit 204 according to Embodiment 2 newly includes, in place of the maximum value calculation unit 304 in FIG. 5, a minimum value calculation unit 401 which calculates a minimum value of the signal level inputted from the input terminal 302 according to an output result of a start-of-section-detection determination unit 303. Then, a reverberation section determination unit 402 according to Embodiment 2 determines a reverberation section from an output of the input terminal 302 and an output of the minimum value calculation unit 401.

Figure 10:
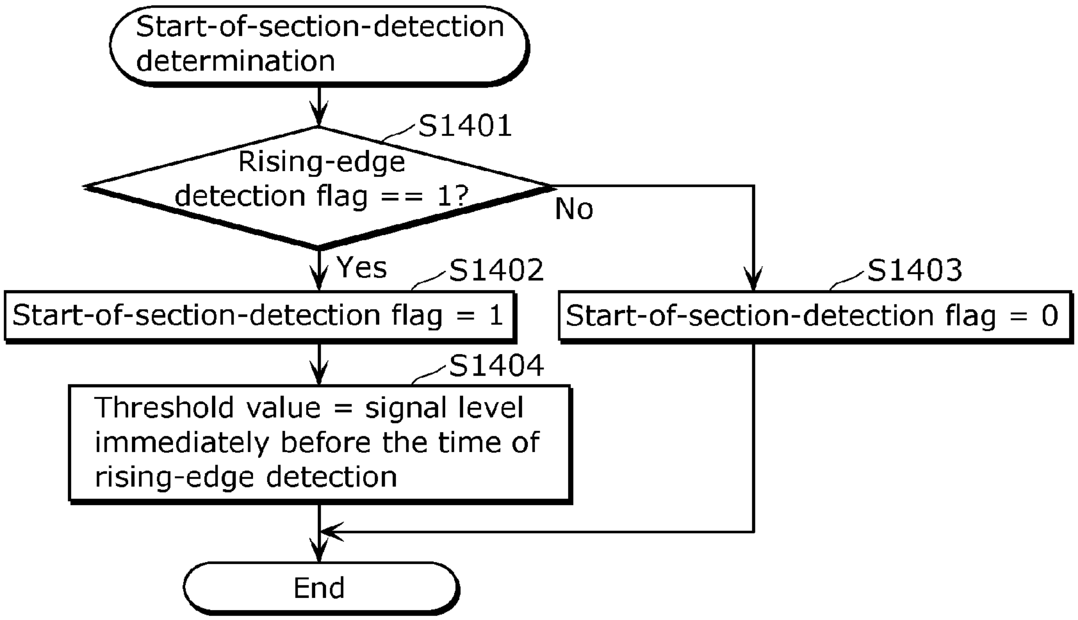
FIG. 10 is a flowchart illustrating operation of a signal section detection unit of the howling suppression device in Embodiment 2 of the present invention.
Figure 10:
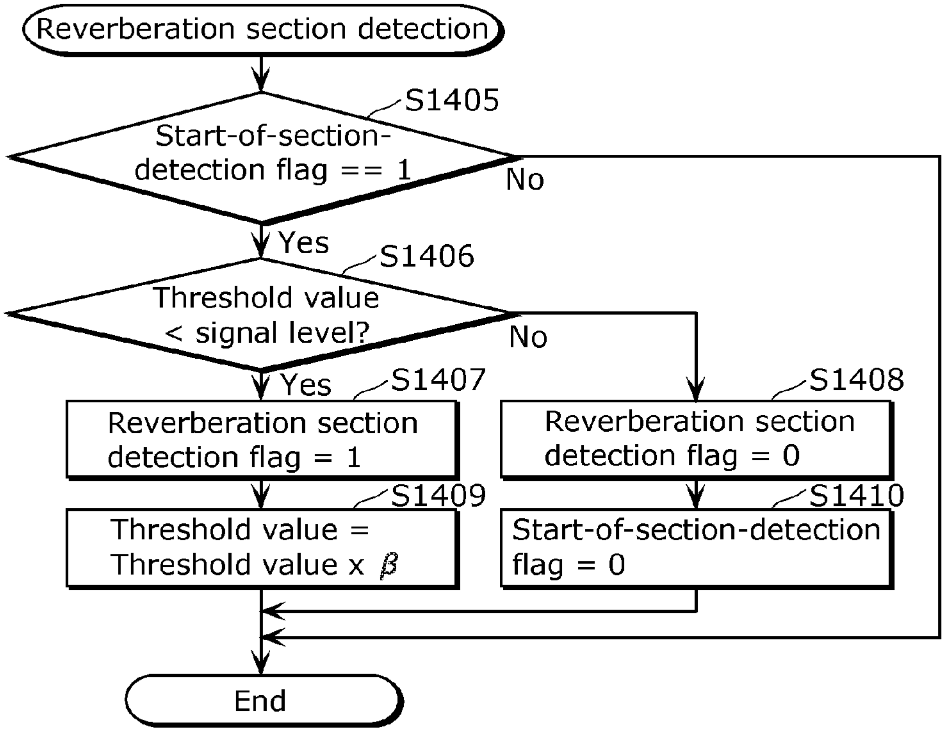

FIG. 10 is a flowchart illustrating operation of the reverberation section detection unit 204 in FIG. 9. First, the reverberation section detection unit 204 determines whether or not to start detection of a reverberation section as shown in (a) of FIG. 10. At the beginning the start-of-section-detection determination unit 303 determines whether or not the value of a rising-edge detection flag is 1 (S1401). When the value of the rising-edge detection flag is 1 (S1401, Yes), the start-of-section-detection determination unit 303 sets a start-of-section-detection flag to 1 (S1202). When the value of the rising-edge detection flag is 0 (S1401, No), the start-of-section-detection determination unit 303 sets the start-of-section-detection flag to 0 (S1403). Moreover, when the value of the rising-edge detection flag is 1 (S1041, Yes), the minimum value calculation unit 401 sets, as a threshold value (a minimum value), the signal level at the time of detection of a rising-edge point (S1404).

Next, the reverberation section determination unit 402 performs detection of a reverberation section as shown in (b) of FIG. 10. First, the reverberation section determination unit 305 checks the value of the start-of-section-detection flag (S1405). The value has been determined in (a) of FIG. 10. When the value of the start-of-section-detection flag is 0 (S1405, No), the reverberation section determination unit 402 ends the processing without determining a reverberation section. When the value of the start-of-section-detection flag is 1 (S1405, Yes), the reverberation section determination unit 402 determines which is greater, the threshold value or the value of the signal level (S1406).

Then, when the threshold value is below the signal level of the input signal (S1406, Yes), the reverberation section determination unit 402 sets the value of the reverberation section detection flag to 1 (S1407). Moreover, the reverberation section determination unit 405 multiplies the threshold value by a constant which is greater than 1 to make it a new threshold value for the next step (S1409). When the threshold value is above the signal level of the input signal (S1406, No), the reverberation section determination unit 405 sets the value of the reverberation section detection flag to 0 (S1408). In this case, the reverberation section determination unit 402 determines that the reverberation section has ended, and sets the value of the start-of-section-detection flag to 0 (S1410).

Figure 11:
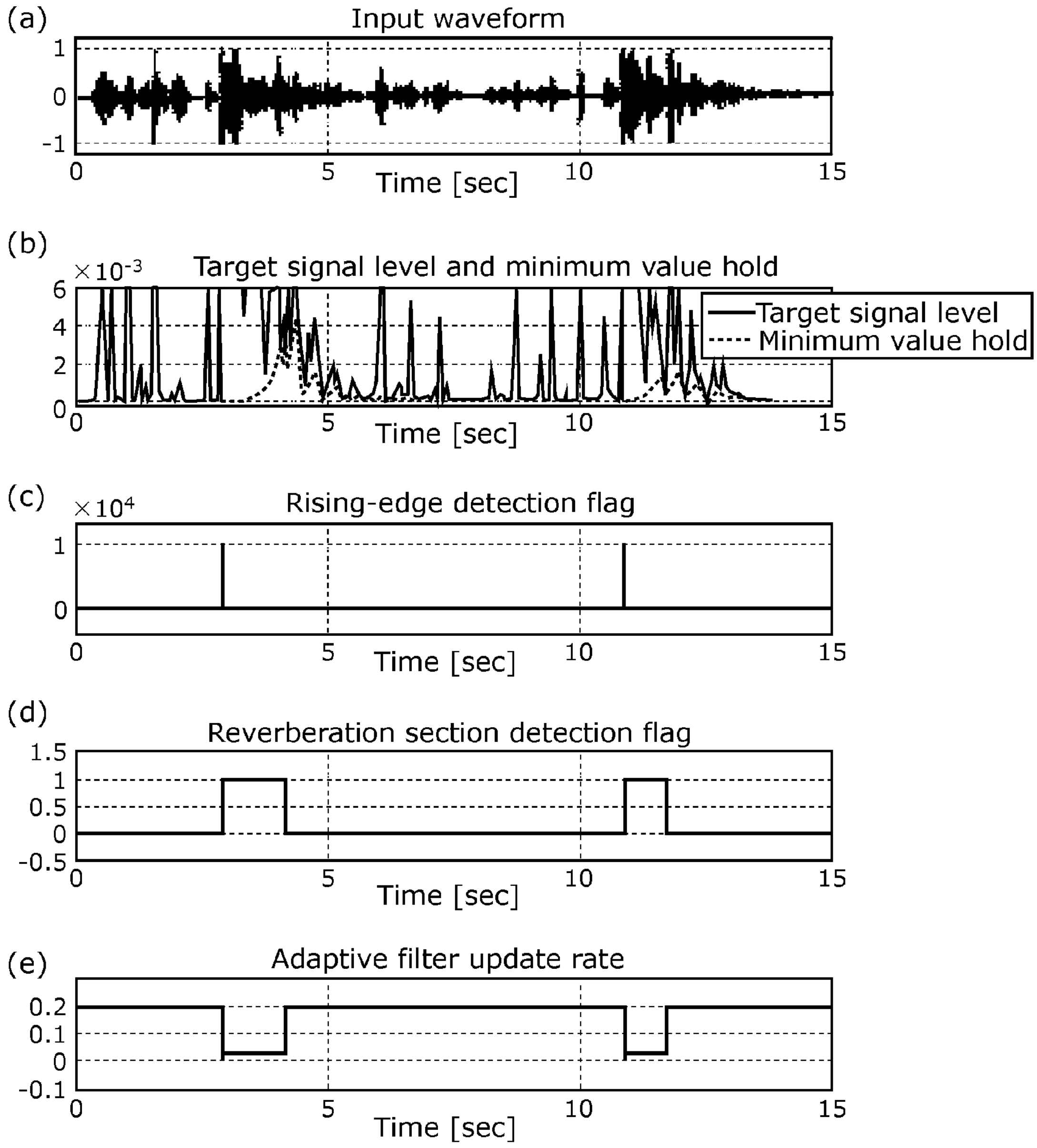
FIG. 11 is a graph illustrating procedures of update control of the howling suppression device in Embodiment 2.

FIG. 11 shows in graph form the procedures in order from detection of a transient signal to control of an update rate.

First, the signal-rising-edge detection unit 203 performs detection of a transient signal on the input signal shown in (a) of FIG. 11 to determine a starting point of a sinusoidal signal. To be specific, the signal-rising-edge detection unit 203 sets the rising-edge detection flag to 1 when a gradient value of the signal level between two different time points, time (t) and time (t−n), exceeds a predetermined threshold value, and sets the rising-edge detection flag to 0 when the gradient value is less than the threshold value. An example of transition of the rising-edge detection flag is shown in (c) of FIG. 11.

Next, the reverberation section detection unit 204 detects a reverberation section of a sinusoidal signal in particular. To be specific, the reverberation section determination unit 402 compares the signal level of a target signal calculated by the level calculation unit 202 with the value of a minimum value hold (which corresponds to a threshold value set in Step S1404 of (a) of FIG. 10 or in Step S1409 of (b) of FIG. 6) of the target signal level, as shown in (b) of FIG. 11. Since the reverberation section of a sinusoidal signal is inputted in such a way to immediately follow a transient signal, it is possible to detect the section by comparing the target signal level and the minimum value of the signal level.

To be specific, the reverberation section determination unit 402 takes advantage of the fact that the signal level in a reverberation section lowers with time to determine, as a section in which the reverberation component continues, a period in which the signal level continues to gradually decreases and the value of the minimum value hold gradually increases without a reversal in the magnitude relationship therebetween. Then, the reverberation section determination unit 402 sets the reverberation section detection flag to 1 in the section from immediately after a transient noise detection flag is turned to 1 to a reversal in the magnitude relationship between the values of the minimum value hold and the value of the signal level. An example of transition of the reverberation section detection flag is shown in (d) of FIG. 11.

Next, the state determination unit 205 receives input of a rising-edge detection flag and a reverberation section detection flag. Although it has been already mentioned that a reverberation component of a sinusoidal signal deteriorates accuracy in estimation accuracy of spatial transfer characteristics by the adaptive filter 107 using the filter coefficient, it has been also confirmed that the accuracy in estimation of spatial transfer characteristics by the adaptive filter 107 using the filter coefficient deteriorates due to an abrupt change in the input level when a transient signal is inputted as well. Therefore, the state determination unit 205 sets the control flag to 1 such that updating of the filter coefficient is stopped or decelerated when at least one of the rising-edge detection flag and the reverberation section detection flag is 1.

Next, the update rate control unit 206 controls the update rate of the adaptive filter 107 according to the value of an inputted control flag. To be specific, the update rate control unit 206 sets the update rate of the adaptive filter 107 to 0 when the value of the control flag is 1 and the update is to be stopped, sets the update rate to a deceleration value when the update is to be decelerated, and sets the update rate to a normal value when the value of the control flag is 0. An example of transition of the update rate is shown in (e) of FIG. 11. Then, the set update rate is outputted from the output terminal 207 to the adaptive filter 107.

In such a configuration, the signal-rising-edge detection unit 203 can detect a transient signal and the reverberation section detection unit 204 can detect the reverberation section of a sinusoidal signal, so that it is possible to determine that a signal for which updating of the filter coefficient of the adaptive filter 107 is not appropriate has been inputted. As a result of that, it is possible to appropriately adjust the update rate of the filter coefficient of the adaptive filter 107 in response to the input signal.

Note that although the reverberation section detection unit 204 according to Embodiment 1 changes only the maximum value in a predetermined range to detect a reverberation section, and the reverberation section detection unit 204 according to Embodiment 2 changes only the minimum value of a predetermined range to detect a reverberation section, these may be combined. Specifically, the reverberation section detection unit 204 may gradually narrow the predetermined range (by gradually decreasing the maximum value and also gradually increasing the maximum value) with time, when determining whether or not the signal level of an input signal is included in a predetermined range.

Embodiment 3

A coefficient update control unit according to Embodiment 3 further includes a level determination unit configured to determine, on a per-unit time basis in a reverberation section, whether or not the signal level of an input signal exceeds a predetermined value. In a reverberation section, an update rate control unit is configured to set an update rate to a first rate while the signal level of the input signal exceeds a predetermined value, and to a second rate while the signal level of the input signal is equal to or below the predetermined value.

Figure 12:
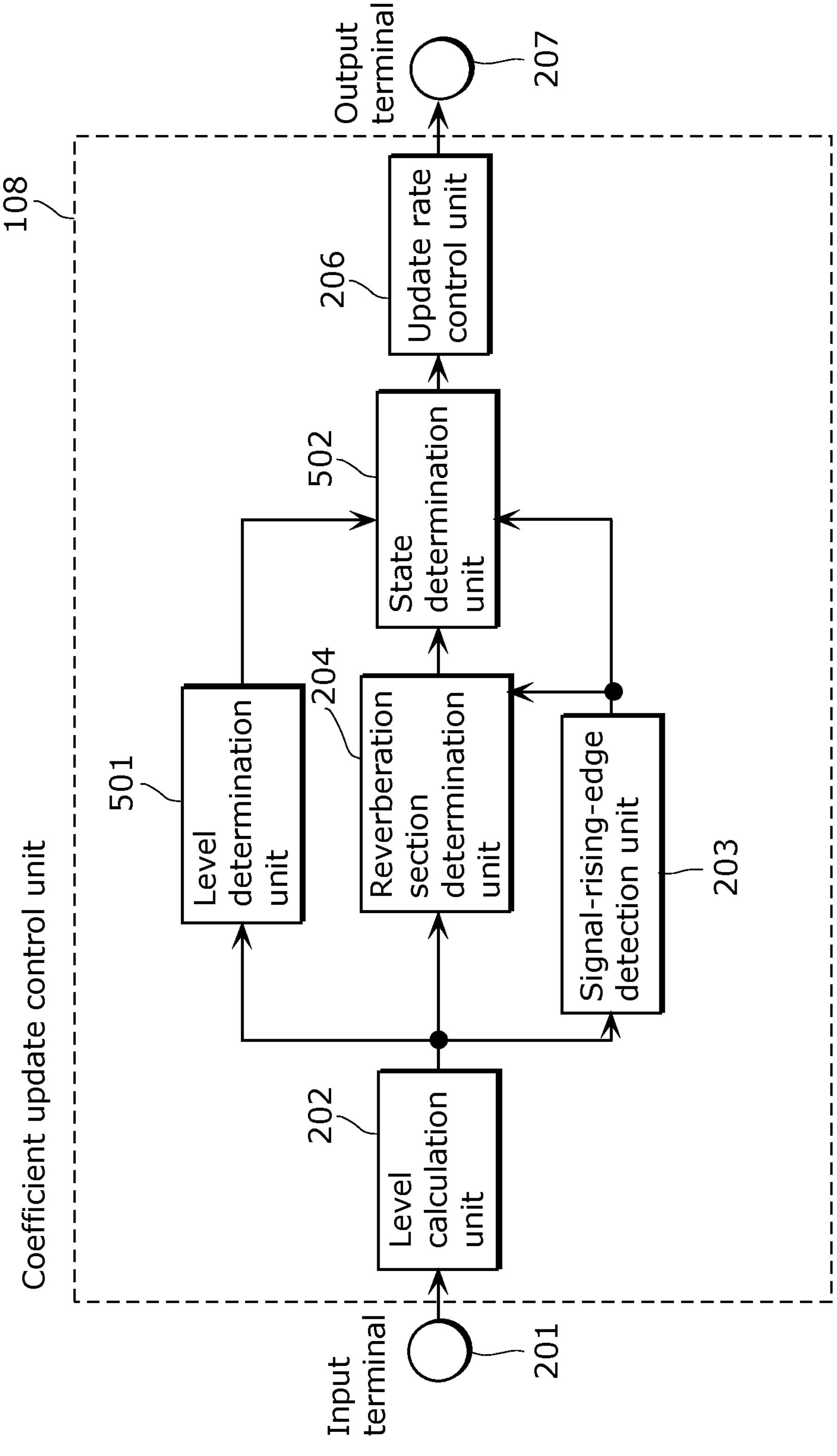
FIG. 12 is a detailed block diagram of a coefficient update control unit of a howling suppression device in Embodiment 3.

Referring to FIG. 12, the coefficient update control unit according to Embodiment 3 will be described in detail. FIG. 12 is a detailed block diagram of the coefficient update control unit 108 of the howling suppression device in Embodiment 3 of the present invention. Note that in FIG. 12, like components as those of FIG. 2 are given like reference signs thereby omitting the description thereof.

In FIG. 12, the coefficient update control unit 108 of the howling suppression device according to Embodiment 3 newly includes a level determination unit 501 which determines, on a per-unit time basis in a reverberation section, whether or not the signal level outputted from a level calculation unit 202 exceeds a predetermined value (hereinafter referred to as a “threshold value”). The state determination unit 502 according to Embodiment 3 determines whether or not a signal for which updating the filter coefficient of an adaptive filter 107 is not appropriate is included in an input signal, based on the rising-edge detection flag outputted from a signal-rising-edge detection unit 203, a reverberation section detection flag outputted from the reverberation section detection unit 204, and a level determination flag outputted from the level determination unit 501.

Although update of the filter coefficient of the adaptive filter 107 works advantageously when an inputted signal has enough magnitude, update of the filter characteristics will make little difference when an inputted signal is small. Taking advantage of this, the signal level of the input signal is added to the criterion for the determination to be made by the state determination unit 502. To be specific, the level determination unit 501 sets the level determination flag to 1 when the magnitude of the input signal level exceeds a predetermined threshold value, and sets the level determination flag to 0 when the magnitude is equal to or below the threshold value.

The state determination unit 502 receives input of the level determination flag in addition to input of a rising-edge detection flag and a reverberation section detection flag. Only when at least one of the rising-edge detection flag and the reverberation section detection flag is 1 and the value of the level determination flag is 1, the state determination unit 502 sets the control flag to 1 such that updating of the filter coefficient is stopped or decelerated.

Figure 13:
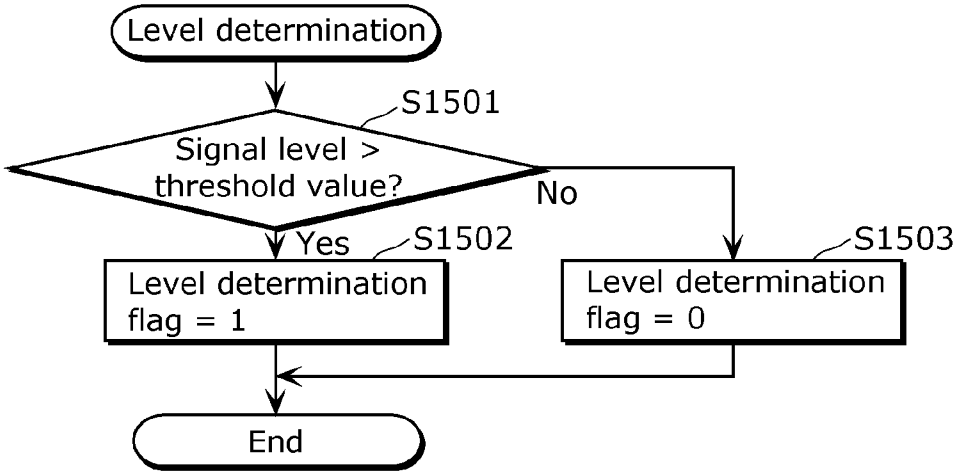
FIG. 13 is a flowchart illustrating operation of a level determination unit of the howling suppression device in Embodiment 3.

FIG. 13 is a flowchart illustrating operation of the level determination unit 501 in FIG. 12. The level determination unit 501 compares the magnitude of an inputted signal level with a threshold value (S1501). Then, the level determination unit 501 sets the level determination flag to 1 when the signal level exceeds the threshold value (S1501, Yes) (S1502), and sets the level determination flag to 0 when the signal level is equal to or below the threshold value (S1501, No) (S1503).

Figure 14:
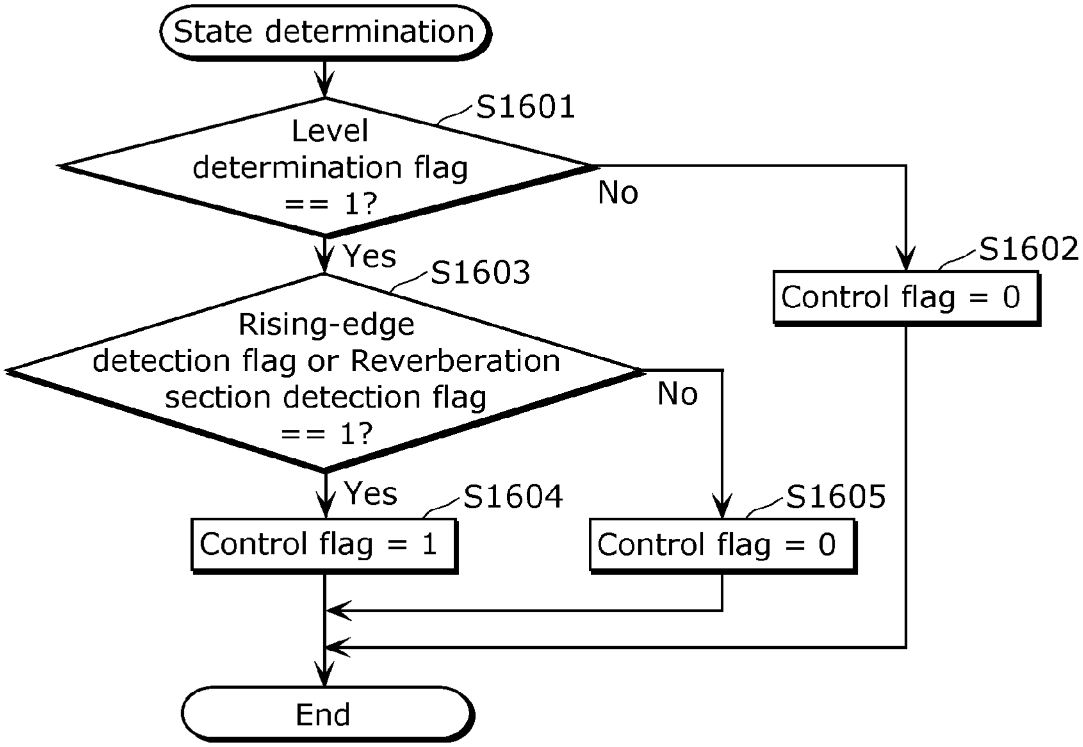
FIG. 14 is a flowchart illustrating operation of a state determination unit of the howling suppression device in Embodiment 3.

FIG. 14 is a flowchart illustrating operation of the state determination unit 502 in FIG. 12. First, the state determination unit 502 checks the value of the level determination flag (S1601). When the value of the level determination flag is 0 (S1601, No), the state determination unit 502 sets the value of the control flag to 0 (S1602) and ends the processing. When the value of the level determination flag is 1 (S1601, Yes), the state determination unit 502 checks the rising-edge detection flag and the reverberation section detection flag (S1603). When at least one of the rising-edge detection flag and the reverberation section detection flag has a value of 1 (S1603, Yes), the state determination unit 502 sets the value of the control flag to 1 (S1604). When both of the rising-edge detection flag and the reverberation section detection flag has a value of 0 (S1603, No), the state determination unit 502 sets the control flag to 0 (S1605).

In this configuration, the level determination unit 501 newly provided outputs flag information to the state determination unit 502, so that updating can be continued even for a small input signal, which is not likely to adversely affect the adaptive filter 107. As a result, the adaptive filter 107 can estimate the spatial transfer characteristics without interruption.

Although it has been described in Embodiment 3 that the level determination flag is set to 1 by the level determination unit 501 when the signal level exceeds a threshold value, configuration may be made such that the determination flag is set to 1 when the state in which the signal level exceeds the threshold value lasts for a predetermined time period.

Embodiment 4

A coefficient update control unit according to Embodiment 4 further includes a frequency analysis unit configured to convert the signal level of an input signal into a frequency signal, and a peak detection unit configured to determine whether or not the frequency signal has a peak. When the frequency signal has a plurality of the peaks, the update rate control unit is configured to set the update rate in the reverberation section to the first rate, and sets the update rate in a section other than the reverberation section to the second rate.

Figure 15:
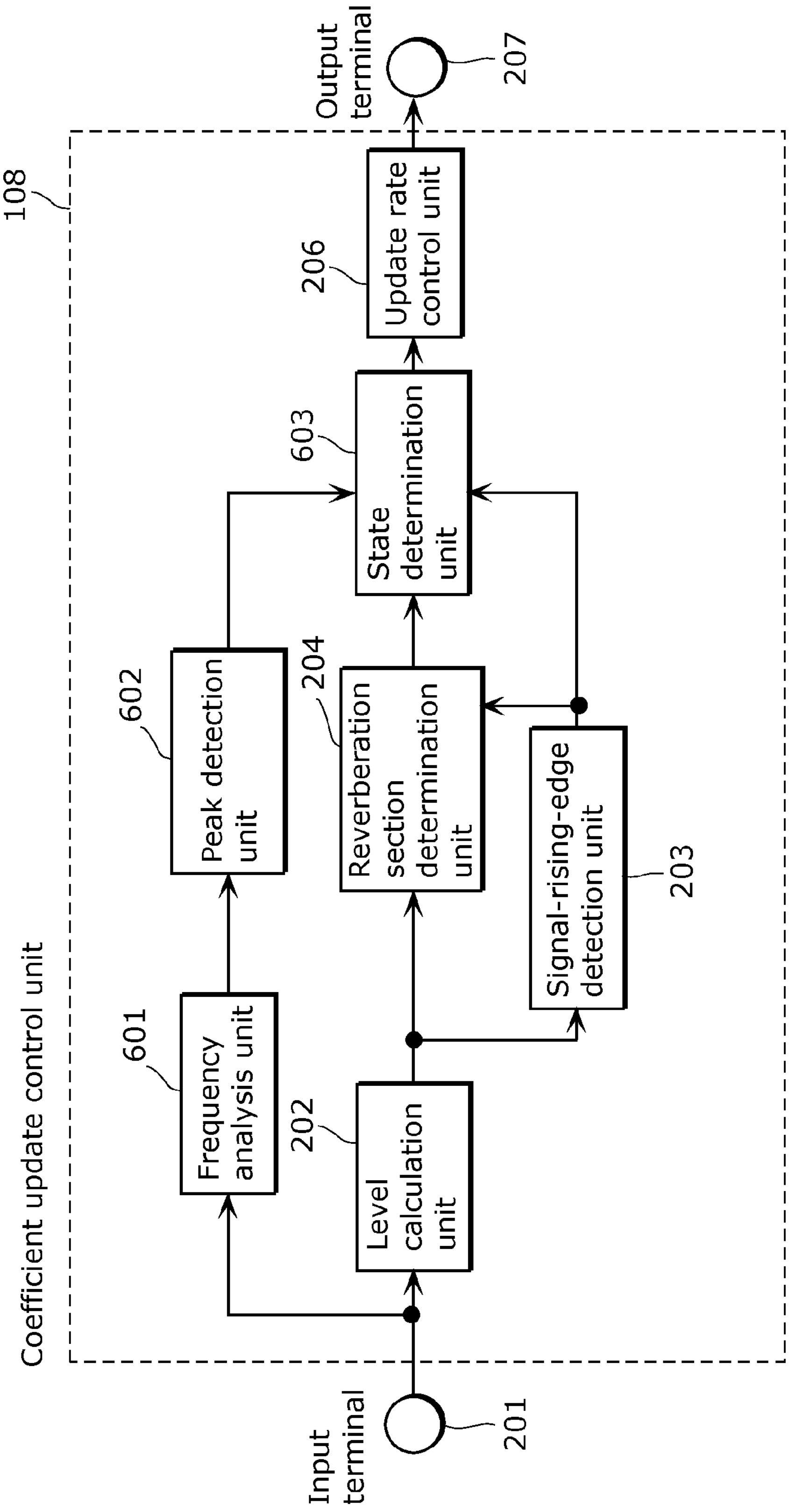
FIG. 15 is a detailed block diagram of a coefficient update control unit of a howling suppression device in Embodiment 4.

Referring to FIG. 15, the coefficient update control unit according to Embodiment 4 will be described in detail. FIG. 15 is a detailed block diagram of the coefficient update control unit 108 of the howling suppression device in Embodiment 4 of the present invention. Note that in FIG. 15, like components as those of FIG. 2 are given like reference signs thereby omitting the description thereof.

In FIG. 15, the coefficient update control unit 108 according to Embodiment 4 newly includes a frequency analysis unit 601 which converts an inputted signal into a signal in the frequency domain, and a peak detection unit 602 which detects a peak of the signal in the frequency domain acquired from the frequency analysis unit 601. Then, the state determination unit 603 according to Embodiment 4 determines whether or not a signal for which updating the filter coefficient of the adaptive filter 107 is inappropriate is included in the input signal, based on inputs of a peak detection flag which is an output result of the peak detection unit 602, a rising-edge detection flag which is an output result of the signal-rising-edge detection unit 203, and a reverberation section detection flag which is an output result of the reverberation section detection unit 204.

The frequency analysis unit 601 divides the input signal acquired from the microphone 101 through the input terminal 201 into a plurality of subband signals by performing frequency transformation. As the frequency transformation method, a known method for dividing a time signal into a plurality of subband signals are used, such as a fast Fourier transformation or a filter bank made up of a plurality of FIR filters or IIR filters. The peak detection unit 602 analyzes frequency characteristics of the subband signals in the frequency domain to detect frequency peaks. Finally, the state determination unit 603 determines whether or not a sinusoidal signal is present in the signal inputted to the microphone 101, based on three parameters: a peak detection flag which is an output result of the peak detection unit 602, a rising-edge detection flag which is an output result of the signal-rising-edge detection unit 203, and a reverberation section detection flag which is an output result of the reverberation section detection unit 204.

A signal of a howling sound is similar to a sine wave having only one sharp frequency peak. In contrast, many sinusoidal signals of sounds which are heard in everyday life (a sound of a wind-bell, a bell, a door bell, etc) characteristically have two or more signal peaks similar to that of sine waves. Taking advantage of this characteristic, it is possible to determine an input signal as having a sinusoidal signal which is not a signal of a howling sound when analysis of frequency characteristics of the input signal shows that the input signal has two or more sharp peaks.

In this configuration, the determination is made by taking into consideration information on frequency peaks included in an input signal, so that a reverberation section of a sinusoidal signal can be detected with accuracy.

Figure 16:
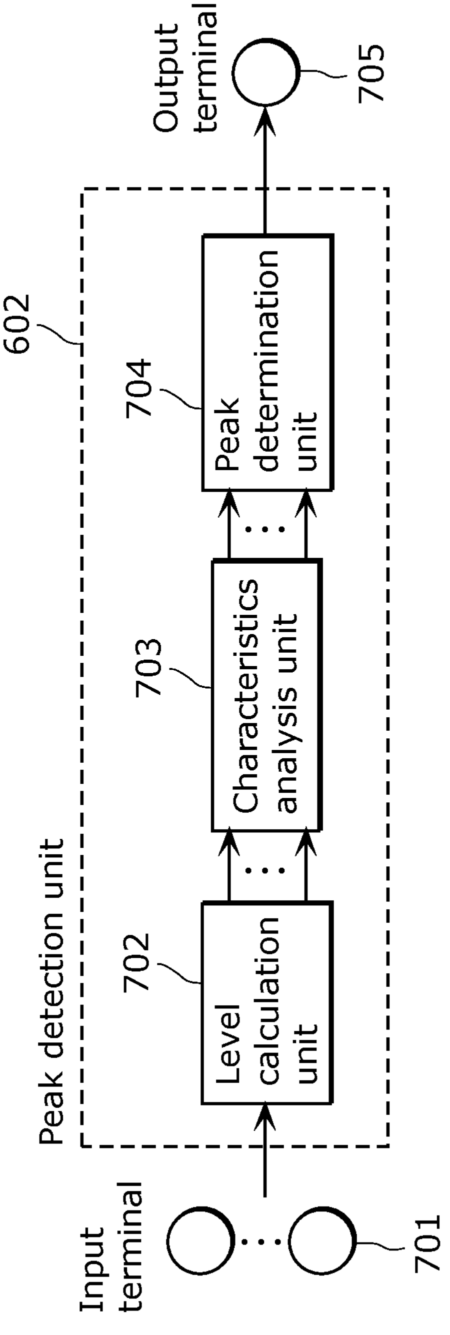
FIG. 16 is a detailed block diagram of a peak detection unit of the howling suppression device in Embodiment 4.

FIG. 16 is a detailed block diagram of the peak detection unit 602 in Embodiment 4 of the present invention.

In FIG. 16, the peak detection unit 602 according to the present embodiment includes: an input terminal 701 which inputs a subband signal in each frequency domain to the peak detection unit 602; a level calculation unit 702 which calculates the signal level of the input signal of each band; a characteristics analysis unit 703 which analyzes characteristics of the input signal from the levels of the signals of the plurality of bands; a peak determination unit 704 which detects a frequency peak of the signal based on output from the characteristics analysis unit 703; and an output terminal 705 which outputs an output result of the peak determination unit 704.

The subband signals in the frequency domain, which have been divided by the frequency analysis unit 601 shown in FIG. 15, are inputted to the level calculation unit 702 for each subband. The level calculation unit 702 calculates a signal level of the inputted frequency signal in each subband. The characteristics analysis unit 703 analyzes the frequency characteristics from the inputted signal level in each subband. To be specific, the characteristics analysis unit 703 calculates and outputs a level ratio of the signal levels between adjacent subbands. The peak determination unit 704 compares the level ratio, which is the output result of the characteristics analysis unit 703, with a threshold value and determines that a sinusoidal signal is present when there is a subband for which the level ratio exceeds the threshold value, and increments a peak-number counter by one. The output terminal 705 outputs a peak detection flag which indicates the value of the peak-number counter.

A signal of a howling sound is similar to a sine wave having one peak. In contrast to this, it is often the case that a sinusoidal signal of a sound which is heard in daily life, such as a sound of a wind-bell, is mixture of sine waves having two or more peaks. Counting the frequency peak numbers of an input signal in this way makes it possible to determine presence or absence of a sinusoidal signal for which updating the filter coefficient of the adaptive filter 107 is inappropriate.

Figure 17:
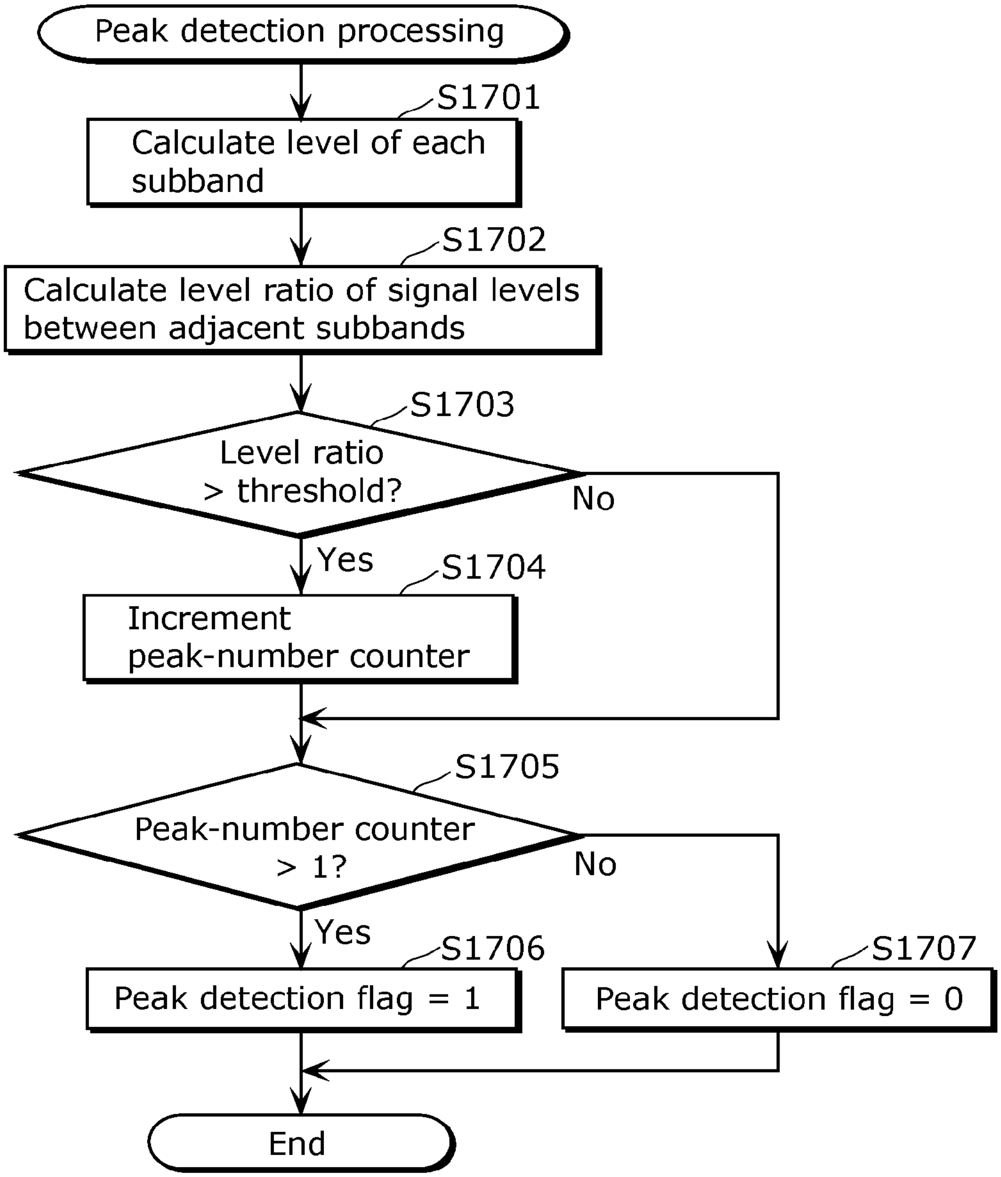
FIG. 17 is a flowchart illustrating operation of the peak detection unit of the howling suppression device in Embodiment 4.

FIG. 17 is a flowchart illustrating operation of the peak detection unit 602 in FIG. 15. First, the level calculation unit 702 calculates a signal level for each subband from a signal in the frequency region inputted to the input terminal 701 (S1701). Next, using the calculated signal levels of the subbands, the characteristics analysis unit 703 calculates a level ratio between adjacent ones of the subbands (S1702). Next, the peak determination unit 704 compares the calculated level ratio with a preset threshold value (S1703). Then, the peak determination unit 704 increments the count value of the peak-number counter by one each time the level ratio exceeds the threshold value (S1703, Yes) (S1704). Finally, the peak determination unit 704 performs peak determination based on the value of the peak-number counter (S1705). Specifically, the peak determination unit 704 determines that the input signal includes sinusoidal signal and sets the value of the peak detection flag to 1 when the value of the peak-number counter exceeds 1 (S1705, Yes) (S1706), and sets the value of the peak detection flag to 0 when the value of the peak-number counter is equal to or less than 1 (S1705, No) (S1707).

Figure 18:
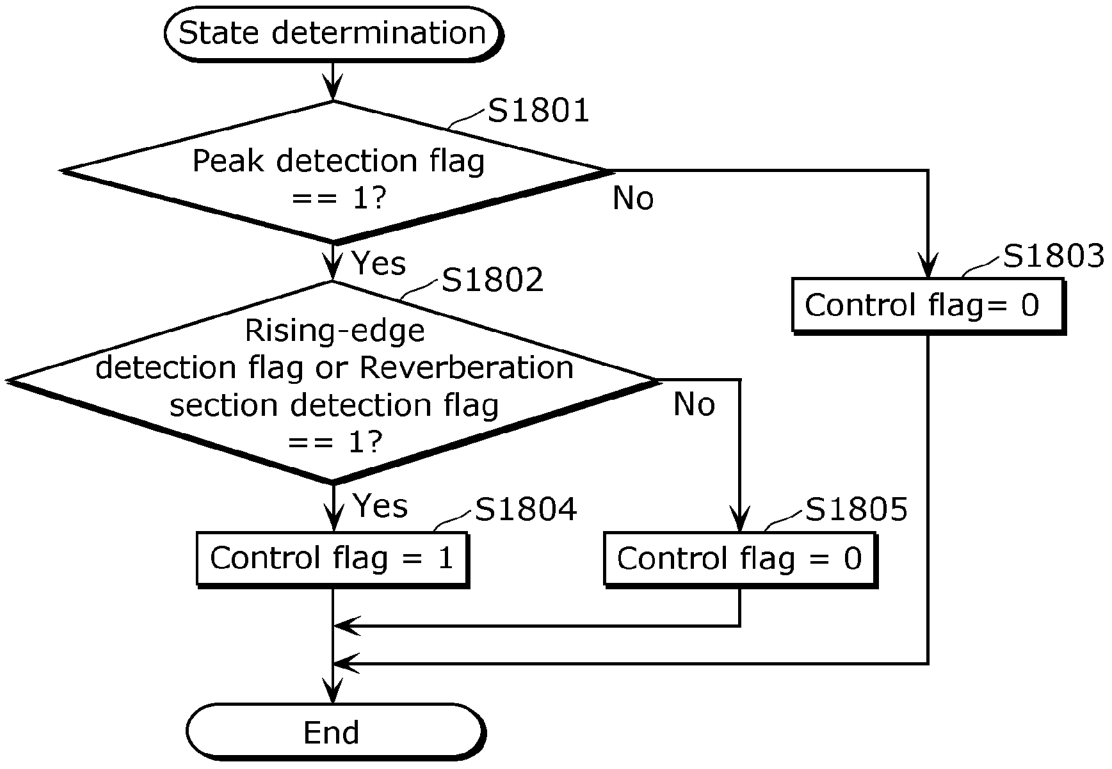
FIG. 18 is a flowchart illustrating operation of a state determination unit of the howling suppression device in Embodiment 4.

FIG. 18 is a flowchart illustrating operation of the state determination unit 605 in FIG. 15. First, the state determination unit 603 performs the processing of determining a peak detection flag (S1801). When the value of the peak detection flag is 0 (S1801, No), the state determination unit 603 sets the value of the control flag to 0 (S1802) and ends the processing. When the value of the peak detection flag is 1 (S1801, Yes), the state determination unit 603 performs the processing of determining a sinusoidal signal using the rising-edge detection flag and the reverberation section detection flag (S1802). When at least one of the rising-edge detection flag and the reverberation section detection flag has a value of 1 (S1802, Yes), the state determination unit 603 sets the value of the control flag to 1 (S1804). When both of the rising-edge detection flag and the reverberation section detection flag has a value of 0 (S1802, No), the state determination unit 603 sets the control flag to 0 (S1805).

In this configuration, detection of peaks in frequency characteristics is performed based on a level ratio of signal levels between subbands so that a sinusoidal signal can be detected more accurately and update of the filter coefficient of the adaptive filter 107 can be controlled appropriately.

Although it has been described in Embodiment 4 that a signal level ratio between adjacent subbands is calculated by the characteristics analysis unit 703, alternatively peak detection may be performed by calculating a difference (level difference) of signal levels between two adjacent subbands or by using magnitude relationship between signal levels of two adjacent subbands.

Moreover, although it has been described that in step S1705 of FIG. 17, the peak detection unit 602 sets the value of the peak detection flag to 1 when the value of the peak-number counter is greater than 1, this is not limiting and the determination threshold value of the peak-number counter may be set to any appropriate value greater than 1. Furthermore, since there may be a case where a sinusoidal signal has no peak, the value of the peak detection flag may be set to 0 when the value of the peak-number counter is 1 and set to 1 when the value of the peak-number counter is other than 1.

The howling suppression device according to each embodiment described above can be utilized in, for example, a hearing aid. To be specific, such a hearing aid includes a sound pickup unit (microphone) which picks up ambient sound and converts it into input signals, the howling suppression device according to any one of the above embodiments, and an output unit (speaker) which converts an error signal produced by a subtractor into an output sound and outputs the sound.

Although the present invention has been described based on the above embodiments, it should be understood that the present invention is not limited to these embodiments. The following is also within the scope of the present invention.

(1) Each of the devices described above can be implemented specifically as a computer system including a microprocessor, a ROM, a RAM, a hard disk unit, a display unit, a keyboard, and a mouse. The RAM or the hard disk unit stores a computer program. The microprocessor operates according to the computer program so that the device performs its function. Here, the computer program includes a combination of instruction codes to indicate instructions to the computer so that the computer performs its predetermined functionality.

(2) All or part of the components of each of the devices may be composed of a system large scale integration (LSI). The system LSI is a super-multifunctional LSI manufactured by integrating constituent units on a single chip, and is specifically a computer system including a microprocessor, ROM, and RAM. The ROM stores a computer program. The microprocessor loads the computer program from the ROM into the RAM and operates according to the loaded computer program so that the system LSI performs its functionality.

(3) All or part of the components of each of the devices may be composed of an IC card or a single-unit module attachable to the devices. Each of the IC card and the module is a computer system including components such as a microprocessor, a ROM, and a RAM. The IC card or the module may include the super-multi-functional LSI mentioned above. The microprocessor operates according to a computer program so that the IC card or the module performs its functionality. The IC card and the module may be tamper-resistant.

(4) The present invention may be implemented as a method described above. Furthermore, the present invention may be implemented as a computer program which causes a computer to execute the method or as a digital signal representing the computer program.

Furthermore, the present invention may be implemented as a computer program or a digital signal recorded on a computer-readable recording medium, such as a flexible disk, a hard disk, a CD-ROM, an MO, a DVD, a DVD-ROM, a DVD-RAM, a Blu-ray Disc (BD), a semiconductor memory, or the like. Furthermore, the present invention may be implemented as a digital signal recorded on any of these recording medium.

Furthermore, the present invention may be implemented as a computer program or a digital signal transmitted through an electric communication line, a wireless or wired communication line, a network typified by the Internet, data broadcasting, or the like.

Furthermore, the present invention may be implemented as a computer system including a microprocessor and memory, in which the memory stores a computer program and the microprocessor operates according to the computer program.

Furthermore, the program or the digital signal may be recorded on the recording medium and transmitted or may be transmitted via the network to be executed on a different independent computer system.

(5) The above embodiments and the variations may be selectively combined.

Although the embodiments of the present invention are described with reference to the drawings, the present invention is not limited to the embodiments shown in the drawings. Various modifications and variations of the embodiments shown in the drawings are covered by the present invention as long as they are the same as or equivalent to the present invention.

INDUSTRIAL APPLICABILITY

The howling suppression device according to the present invention is applicable to various sound devices having a microphone and a speaker and is useful as a howling suppression device which suppresses a howling sound generated by sound coupling between the speaker and the microphone.

REFERENCE SIGNS LIST

101, 801 microphone
102, 802 subtractor
103 sound processing unit
104 amplifier
105, 804 speaker
106, 805 delay unit
107, 806 adaptive filter
108 coefficient update control unit
201, 301, 302, 701 input terminal
202 level calculation unit
203 signal-rising-edge detection unit
204 reverberation section detection unit

205, 502, 603 state determination unit
206 update rate control unit
207, 306, 705 output terminal
303 start-of-section-detection determination unit
304 maximum value calculation unit
305, 402 reverberation section determination unit
401 minimum value calculation unit
501 level determination unit
601 frequency analysis unit
602 peak detection unit
702 level calculation unit
703 characteristics analysis unit
704 peak determination unit
803 hearing-aid processor
807 autocorrelation calculation unit
808 threshold value evaluation unit
809 update control unit

The invention claimed is:

1. A howling suppression device which reduces a howling component included in an input signal, the howling suppression device comprising:

a subtractor which produces an error signal by subtracting, from the input signal, a pseudo feedback signal which is an estimated signal of a feedback signal included in the input signal as the howling component;

an adaptive filter which produces the pseudo feedback signal by applying filtering to the error signal, the produced pseudo feedback signal being to be used for a next input signal; and a coefficient update control unit configured to control an update rate of a filter coefficient of the adaptive filter, wherein the coefficient update control unit includes:

a level calculation unit configured to calculate a signal level of the input signal;

a signal-rising-edge detection unit configured to detect a rising-edge point from which an increase amount of the signal level of the input signal per unit time exceeds a threshold value;

a reverberation section detection unit configured to detect a reverberation section which starts at the rising-edge point and ends at a terminal point at which the signal level of the input signal departs from a predetermined range which gradually narrows with time; and an update rate control unit configured to set the update rate in the reverberation section to a first update rate and the update rate in a section other than the reverberation section to a second update rate which is higher than the first update rate, and the adaptive filter updates the filter coefficient for the application of the filtering to the error signal at either the first or second update rate set by the update rate control unit.

2. The howling suppression device according to claim 1, wherein the coefficient update control unit further includes a level determination unit configured to determine, on a per-unit time basis in the reverberation section, whether or not the signal level of the input signal exceeds a predetermined value, and in the reverberation section, the update rate control unit is configured to set the update rate to the first update rate while the signal level of the input signal exceeds the predetermined value, and to the second update rate while the signal level of the input signal is equal to or below the predetermined value.

3. The howling suppression device according to claim 1, wherein the coefficient update control unit further includes:

a frequency analysis unit configured to convert the signal level of the input signal into a frequency signal; and a peak detection unit configured to determine whether or not the frequency signal has a peak, wherein when the frequency signal has a plurality of the peaks, the update rate control unit is configured to set the update rate in the reverberation section to the first update rate, and set the update rate in a section other than the reverberation section to the second update rate.

4. The howling suppression device according to claim 1, wherein the signal-rising-edge detection unit is configured to detect the rising-edge point by comparing a gradient value of the signal level of the input signal in time direction with the threshold value.

5. The howling suppression device according to claim 1, wherein the signal-rising-edge detection unit is configured to detect the rising-edge point by comparing a differential value of the signal level of the input signal in time direction with the threshold value.

6. The howling suppression device according to claim 1, wherein the reverberation section detection unit further includes:

a maximum value calculation unit configured to gradually decrease a maximum value of the predetermined range with time; and a reverberation section determination unit configured to determine a point at which the signal level of the input signal reaches the maximum value as the terminal point of the reverberation section.

7. The howling suppression device according to claim 1, wherein the reverberation section detection unit further includes:

a minimum value calculation unit configured to gradually increase a minimum value of the predetermined range with time; and a reverberation section determination unit configured to determine a point at which the signal level of the input signal reaches the minimum value as the terminal point of the reverberation section.

8. A hearing aid comprising:

a sound pickup unit configured to pick up ambient sound and convert the ambient sound into the input signal;

the howling suppression device according to claim 1; and an output unit configured to convert the error signal produced by the subtractor into an output sound and output the output sound.

9. A howling suppression method for reducing a howling component included in an input signal, the howling suppression method comprising:

producing an error signal by subtracting, from the input signal, a pseudo feedback signal which is an estimated signal of a feedback signal included in the input signal as the howling component;

producing the pseudo feedback signal by applying filtering to the error signal, the produced pseudo feedback signal to be used for a next input signal; and controlling an update rate of a filter coefficient for the producing of a pseudo feedback signal, wherein the controlling includes:

calculating a signal level of the input signal;

detecting a rising-edge point from which an increase amount of the signal level of the input signal per unit time exceeds a threshold value;

detecting a reverberation section which starts at the rising-edge point and ends at a terminal point at which the signal level of the input signal departs from a predetermined range which gradually narrows with time; and setting the update rate in the reverberation section to a first update rate and the update rate in a section other than the reverberation section to a second update rate which is higher than the first update rate, and in the producing of a pseudo feedback signal, the filter coefficient for the application of the filtering to the error signal is updated at either the first or second update rate.

10. An integrated circuit which reduces a howling component included in an input signal, the integrated circuit comprising:

a subtractor which produces an error signal by subtracting, from the input signal, a pseudo feedback signal which is an estimated signal of a feedback signal included in the input signal as the howling component;

an adaptive filter which produces the pseudo feedback signal by applying filtering to the error signal, the produced pseudo feedback signal being to be used for a next input signal; and a coefficient update control unit configured to control an update rate of a filter coefficient of the adaptive filter, wherein the coefficient update control unit includes:

a level calculation unit configured to calculate a signal level of the input signal;

a signal-rising-edge detection unit configured to detect a rising-edge point from which an increase amount of the signal level of the input signal per unit time exceeds a threshold value;

a reverberation section detection unit configured to detect a reverberation section which starts at the rising-edge point and ends at a terminal point at which the signal level of the input signal departs from a predetermined range which gradually narrows with time; and an update rate control unit configured to set the update rate in the reverberation section to a first update rate and the update rate in a section other than the reverberation section to a second update rate which is higher than the first update rate, and the adaptive filter updates the filter coefficient for the application of the filtering to the error signal at either the first or second update rate set by the update rate control unit.

* * * * *